US010143812B2

(12) United States Patent
Engelbreth

(10) Patent No.: US 10,143,812 B2
(45) Date of Patent: Dec. 4, 2018

(54) METERED DOSE INHALER APPLICATOR

(71) Applicant: TRUDELL MEDICAL INTERNATIONAL, London (CA)

(72) Inventor: Daniel Engelbreth, London (CA)

(73) Assignee: Trudell Medical International, London (CA)

(*) Notice: Subject to any disclaimer, the term of this patent is extended or adjusted under 35 U.S.C. 154(b) by 548 days.

(21) Appl. No.: 14/849,083

(22) Filed: Sep. 9, 2015

(65) Prior Publication Data

US 2016/0129206 A1  May 12, 2016

Related U.S. Application Data

(63) Continuation of application No. PCT/IB2014/000291, filed on Mar. 11, 2014.

(60) Provisional application No. 61/781,828, filed on Mar. 14, 2013.

(51) Int. Cl.
*A61M 15/00* (2006.01)
*A61M 11/08* (2006.01)
*A61M 11/04* (2006.01)

(52) U.S. Cl.
CPC ........ *A61M 15/0001* (2014.02); *A61M 11/04* (2013.01); *A61M 11/08* (2013.01); *A61M 15/009* (2013.01); *A61M 15/0065* (2013.01); *A61M 2205/276* (2013.01); *A61M 2205/586* (2013.01)

(58) Field of Classification Search
CPC .. A61M 15/0001; A61M 11/04; A61M 11/08; A61M 15/0065; A61M 15/009; A61M 2205/276; A61M 2205/586; A61M 15/0021; A61M 11/02; A61M 15/0086; A61M 2202/064; A61M 15/08; A61M 15/00; A61M 15/0026
USPC ....................................................... 128/200.23
See application file for complete search history.

(56) References Cited

U.S. PATENT DOCUMENTS

| 3,405,843 | A | * | 10/1968 | Watson, Jr. ......... B05B 11/3001 137/846 |
| 3,456,645 | A | | 7/1969 | Brock |
| 3,789,843 | A | * | 2/1974 | Armstrong ........ A61M 15/0091 128/200.23 |
| 4,077,548 | A | * | 3/1978 | Beard ................. B05B 11/3057 222/321.8 |

(Continued)

FOREIGN PATENT DOCUMENTS

| DE | 4436051 A1 | 4/1996 |
| WO | WO 2010/007361 | 1/2010 |

*Primary Examiner* — Andrew S Lo
(74) *Attorney, Agent, or Firm* — Brinks Gilson & Lione

(57) ABSTRACT

A metered dose inhaler ("MDI") applicator is disclosed that includes a carrier, a housing, an adjuster and a lever. The carrier defines an aperture configured to receive a boot of a MDI. The housing is configured to be assembled with the carrier and to move in a vertical direction within the MID applicator relative to the carrier. The adjuster is configured to move between a locked position and an unlocked position, wherein when the adjuster is in the locked position, the adjuster is configured to prevent the carrier and the housing from moving in one or more directions relative to one another. The lever is pivotally connected to the housing and is configured to transfer a force applied to the lever to a canister of the MDI and to actuate the MDI to dispense an aerosolized medicine.

14 Claims, 34 Drawing Sheets

(56) References Cited

U.S. PATENT DOCUMENTS

| | | | | |
|---|---|---|---|---|
| 4,079,862 A * | 3/1978 | Fegley | ................ | B65D 83/267 |
| | | | | 222/162 |
| 4,324,348 A | 4/1982 | Johnson et al. | | |
| 4,402,430 A * | 9/1983 | Fox | ................ | F41H 9/10 |
| | | | | 222/183 |
| 4,678,106 A * | 7/1987 | Newell | ................ | A61M 15/0025 |
| | | | | 222/162 |
| 4,771,769 A * | 9/1988 | Hegemann | ................ | A61M 11/02 |
| | | | | 128/200.22 |
| 4,834,083 A * | 5/1989 | Byram | ................ | A61M 15/009 |
| | | | | 128/200.14 |
| 4,860,738 A | 8/1989 | Hegemann et al. | | |
| 5,027,808 A * | 7/1991 | Rich | ................ | A61M 15/0091 |
| | | | | 128/200.23 |
| 5,487,489 A * | 1/1996 | Weiss | ................ | B05B 11/0037 |
| | | | | 222/1 |
| 5,511,540 A * | 4/1996 | Bryant | ................ | A61M 15/0091 |
| | | | | 128/200.23 |
| 6,397,837 B1 * | 6/2002 | Ferris | ................ | A61M 15/009 |
| | | | | 128/200.14 |
| 6,681,763 B2 * | 1/2004 | Ferris | ................ | A61M 15/009 |
| | | | | 128/200.22 |
| 7,322,355 B2 * | 1/2008 | Jones | ................ | A61M 15/0028 |
| | | | | 128/200.23 |
| 7,467,629 B2 * | 12/2008 | Rand | ................ | A61M 15/009 |
| | | | | 128/200.14 |
| D683,443 S * | 5/2013 | Mullane | ................ | D24/110 |
| 8,578,932 B2 * | 11/2013 | Andersen | ................ | A61M 15/0091 |
| | | | | 128/200.14 |
| 8,695,589 B2 * | 4/2014 | Mullane | ................ | A61M 15/0086 |
| | | | | 128/200.14 |
| 2002/0073992 A1 * | 6/2002 | Andersson | ................ | A61M 15/0091 |
| | | | | 128/200.23 |
| 2005/0066961 A1 * | 3/2005 | Rand | ................ | A61M 15/009 |
| | | | | 128/200.14 |
| 2007/0074718 A1 * | 4/2007 | Austin | ................ | A61M 15/0086 |
| | | | | 128/200.23 |
| 2007/0131717 A1 * | 6/2007 | Davies | ................ | A61M 15/009 |
| | | | | 222/162 |
| 2010/0083963 A1 * | 4/2010 | Wharton | ................ | A45F 5/00 |
| | | | | 128/203.15 |
| 2011/0061646 A1 * | 3/2011 | Crosby | ................ | A61M 15/009 |
| | | | | 128/200.23 |
| 2011/0114089 A1 * | 5/2011 | Andersen | ................ | A61M 15/0091 |
| | | | | 128/200.23 |
| 2011/0155129 A1 * | 6/2011 | Stedman | ................ | A61M 15/009 |
| | | | | 128/200.23 |
| 2013/0061850 A1 * | 3/2013 | Bowman | ................ | A61M 15/009 |
| | | | | 128/200.23 |
| 2013/0139814 A1 * | 6/2013 | Mullane | ................ | A61M 15/0086 |
| | | | | 128/203.12 |
| 2014/0290652 A1 * | 10/2014 | Davies | ................ | A61M 15/009 |
| | | | | 128/203.12 |
| 2015/0053207 A1 * | 2/2015 | Knell | ................ | A61M 15/0013 |
| | | | | 128/203.12 |

* cited by examiner

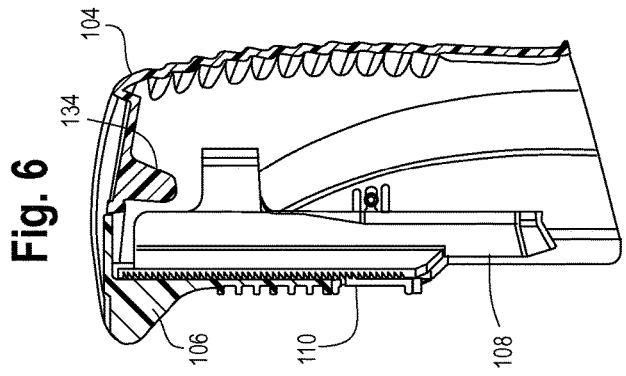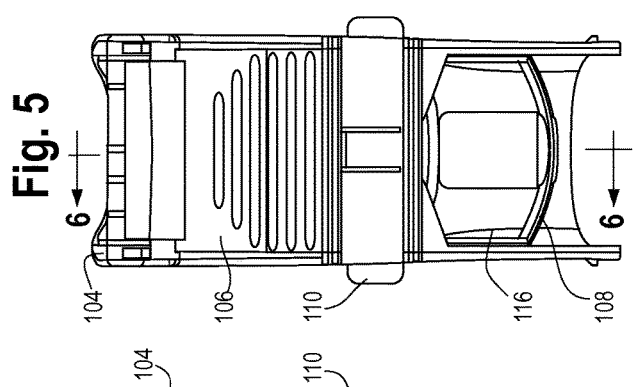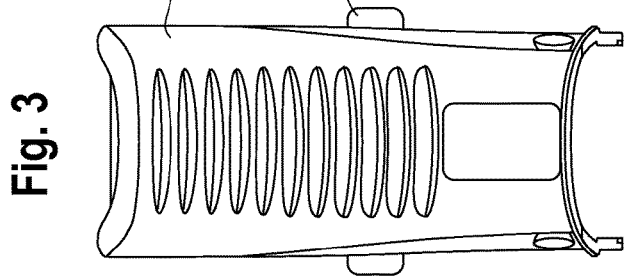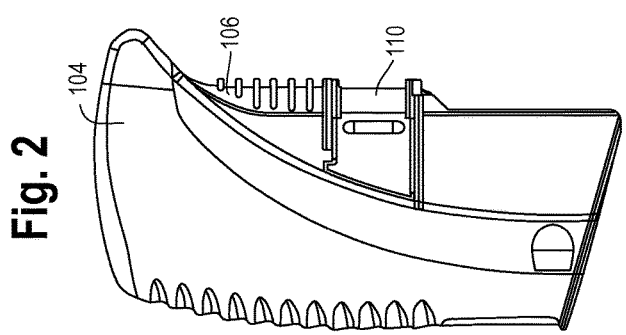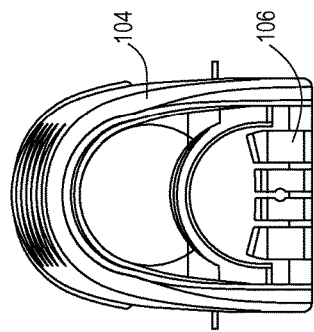

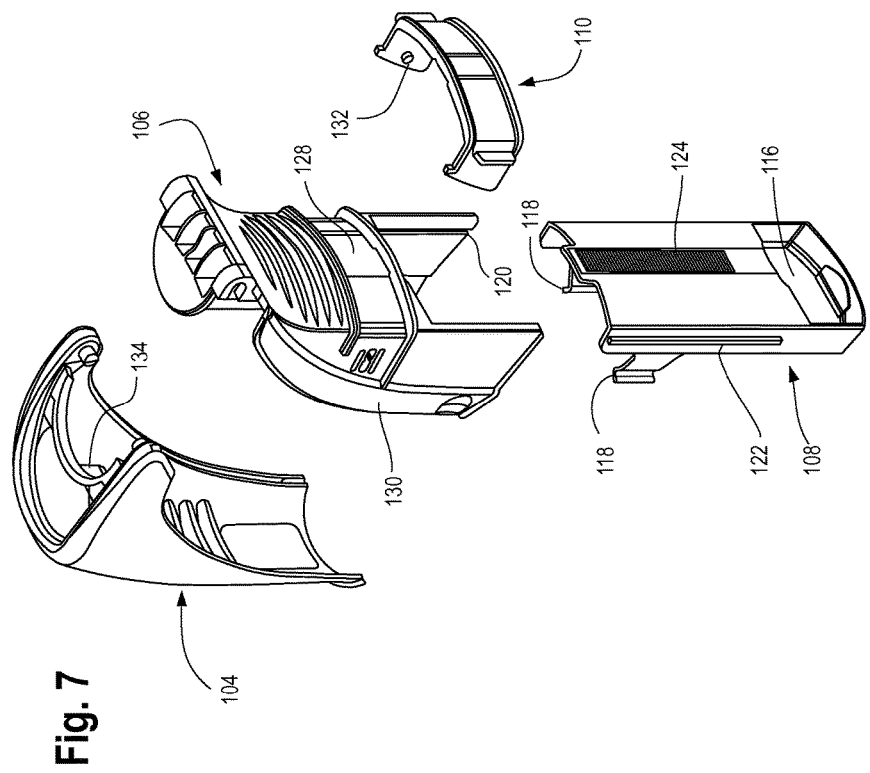

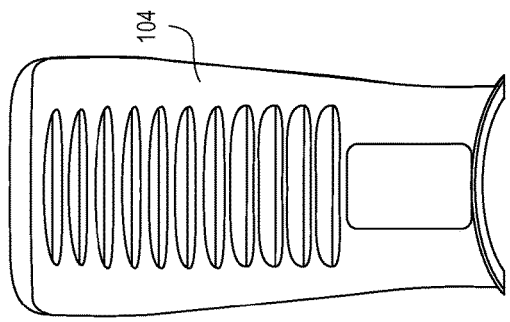
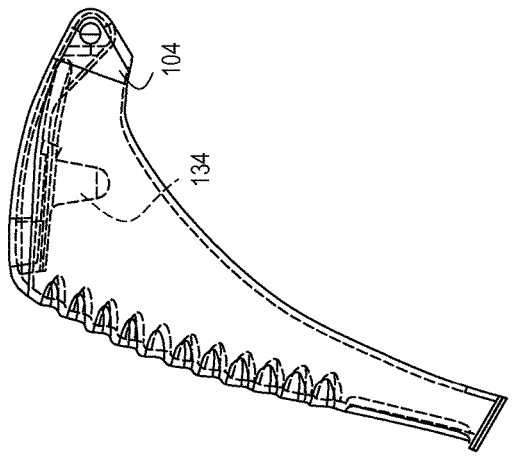
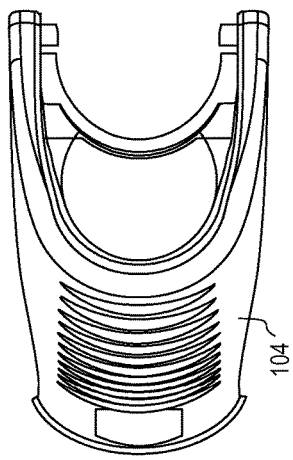
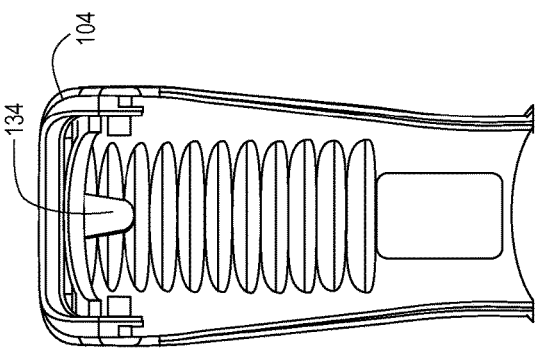

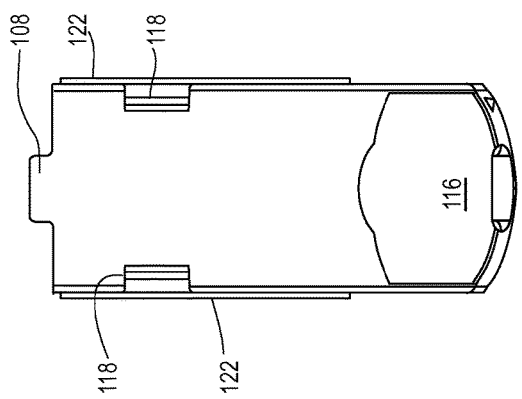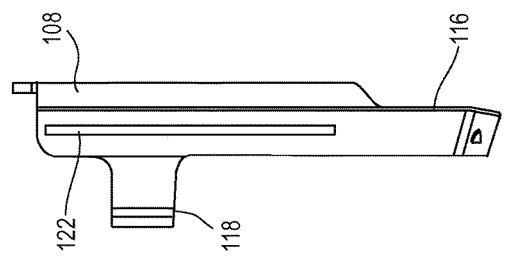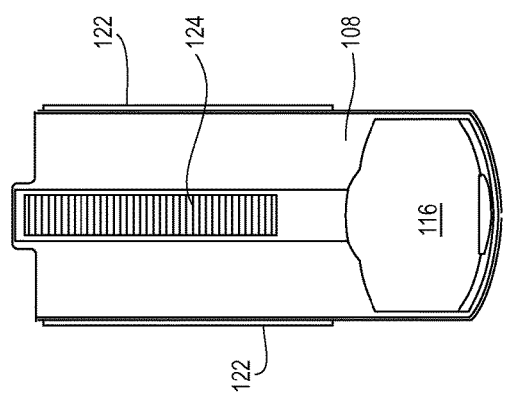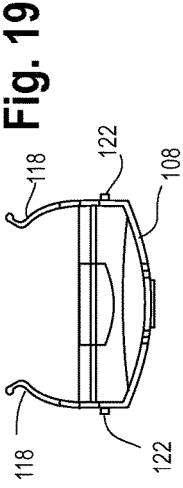

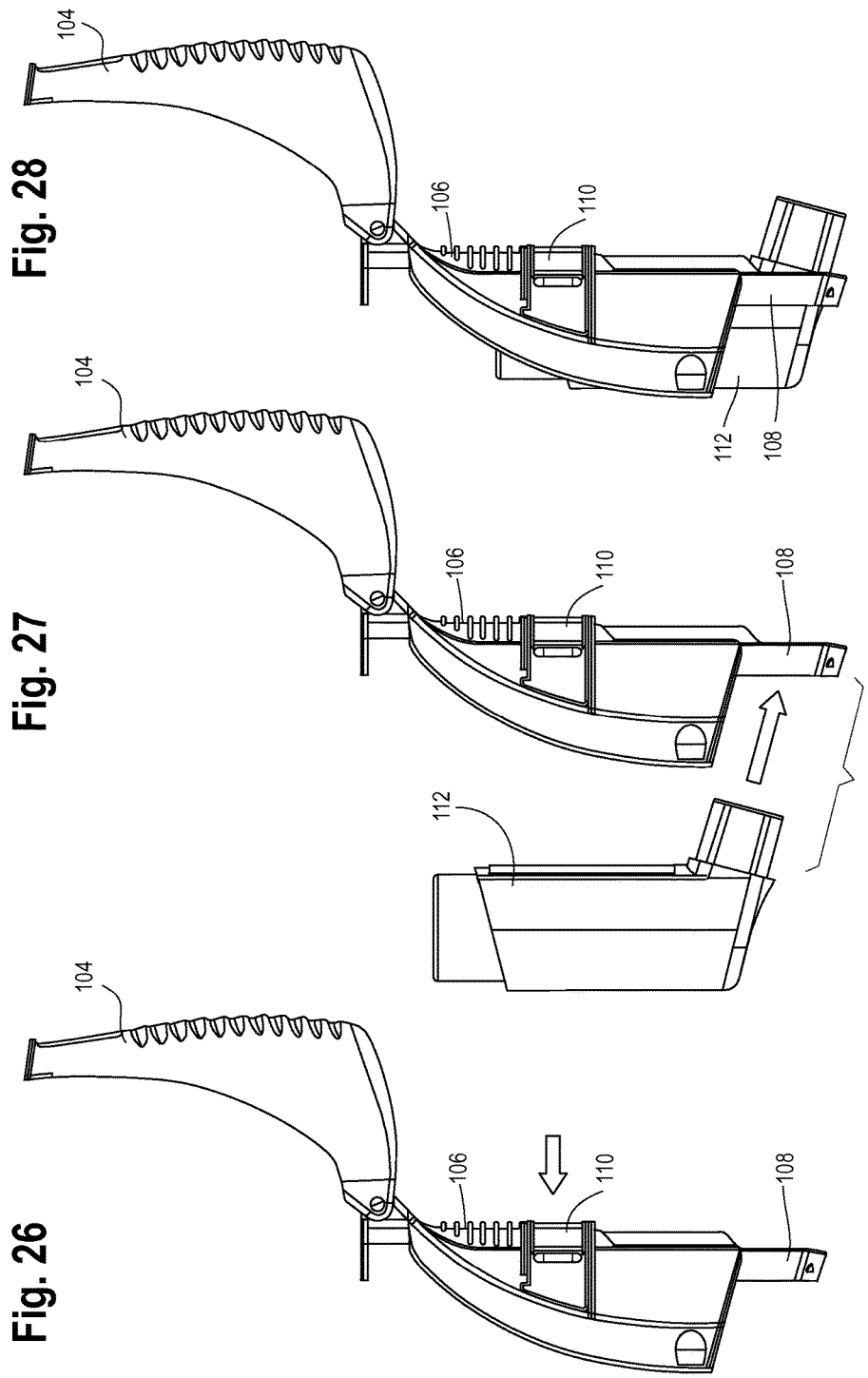

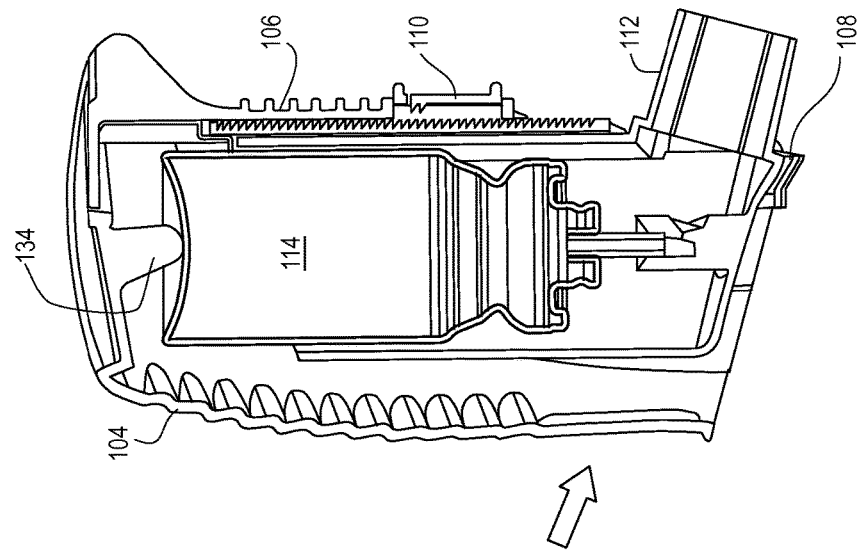
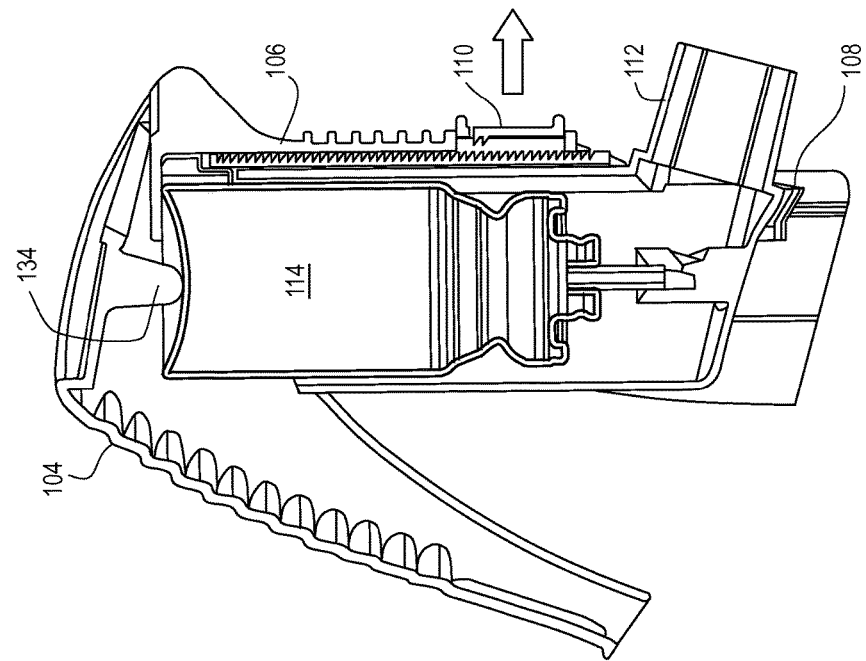

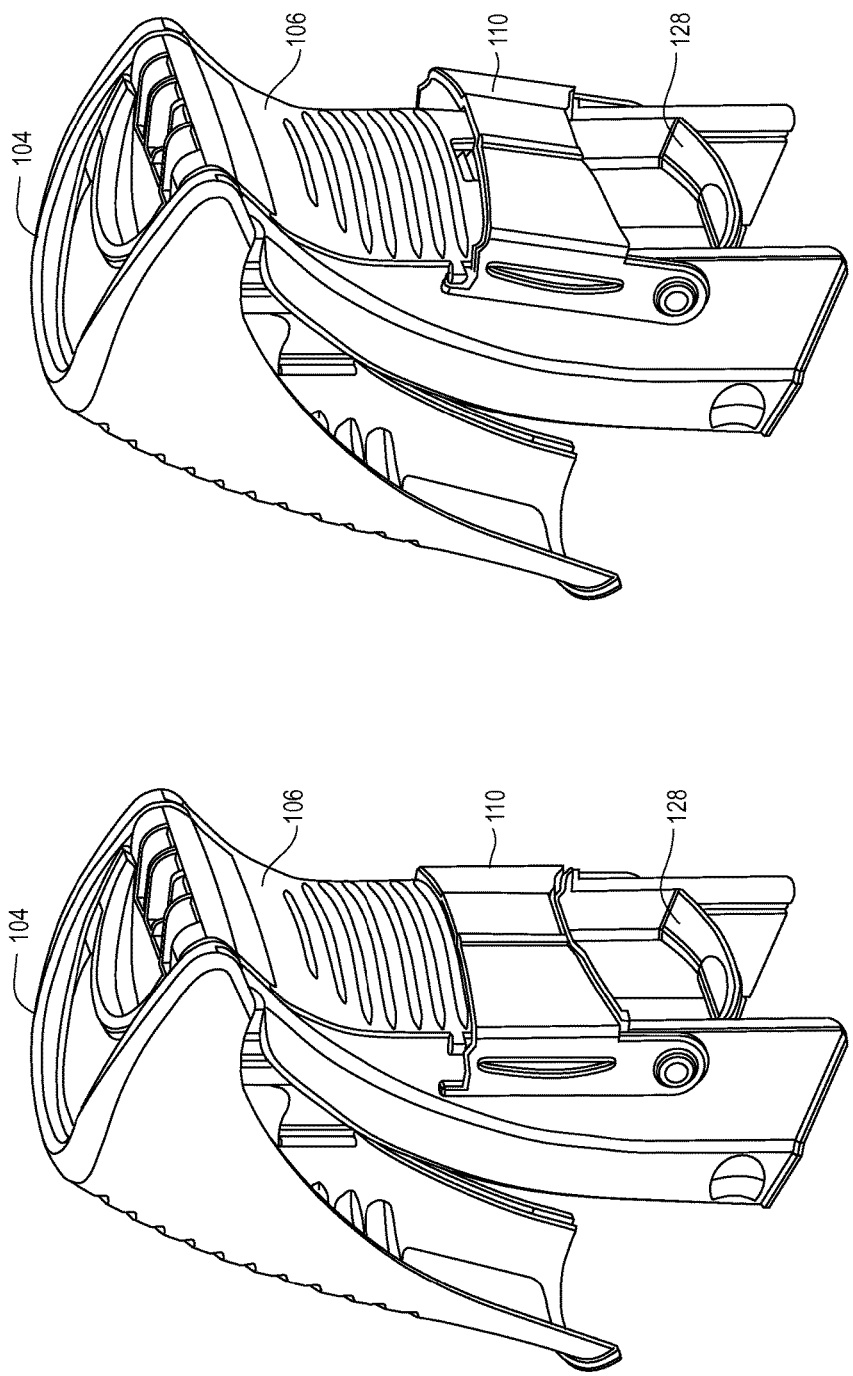

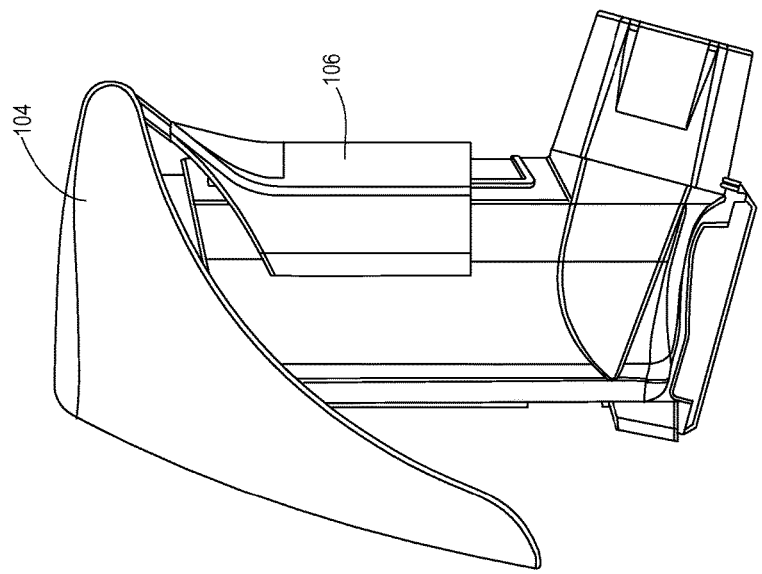
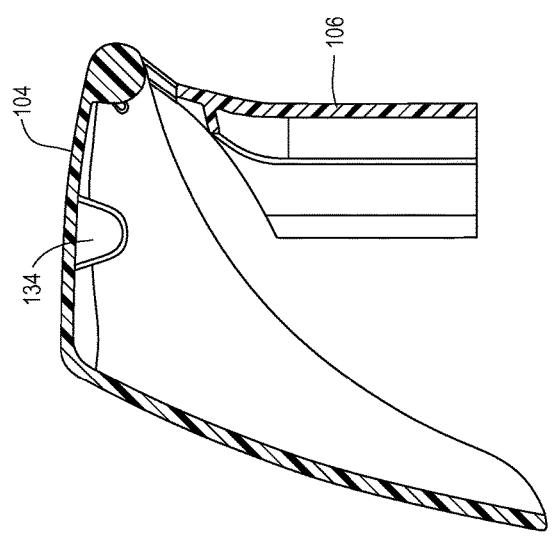

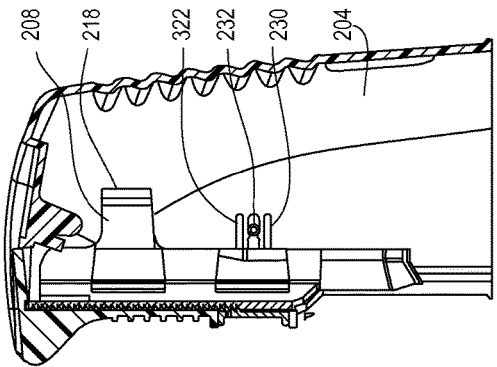
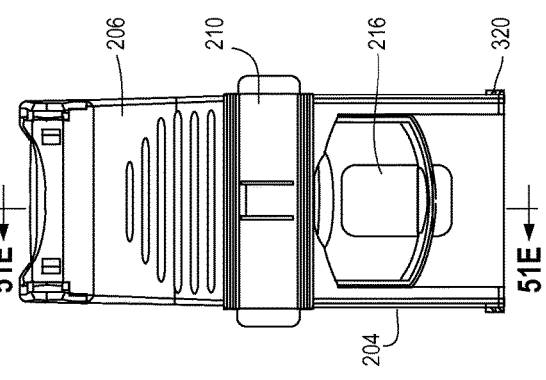
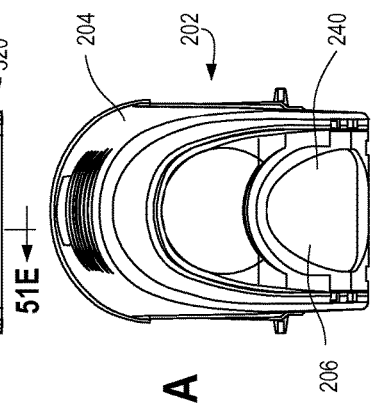
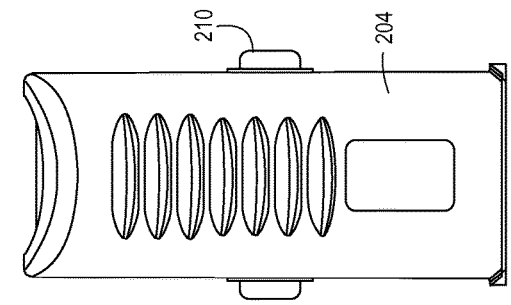
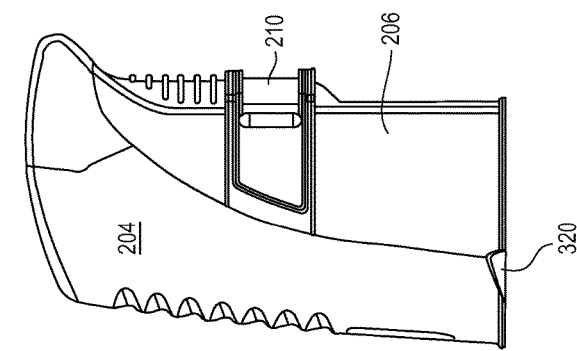

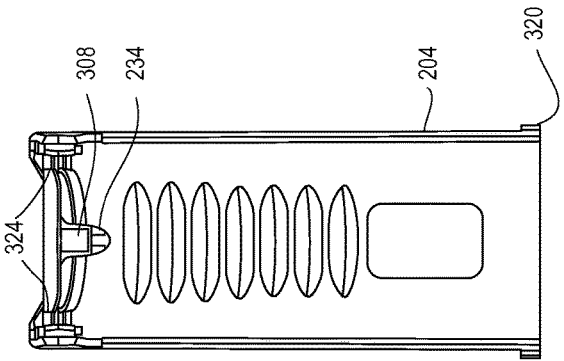
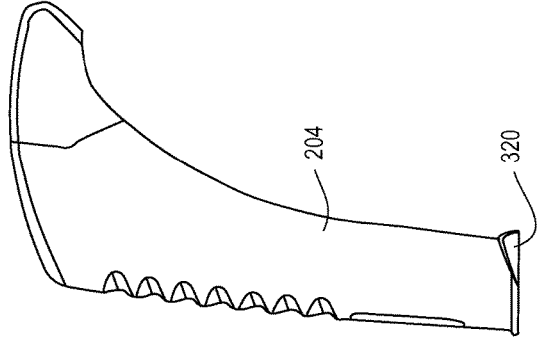
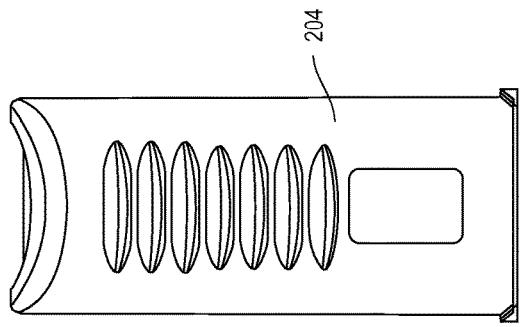
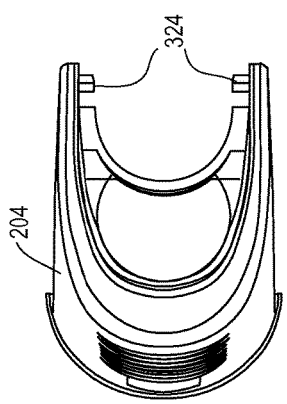

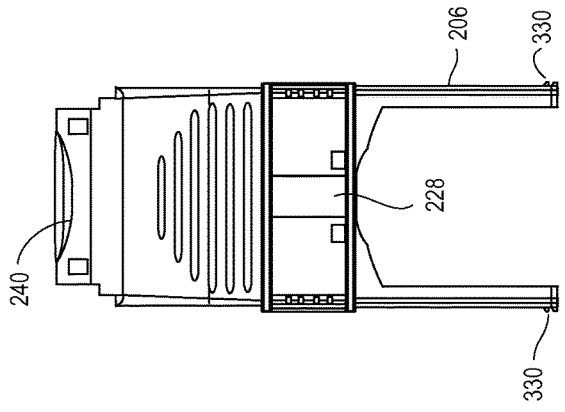
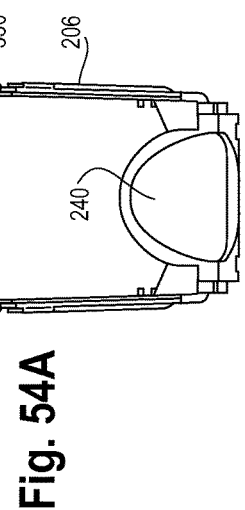
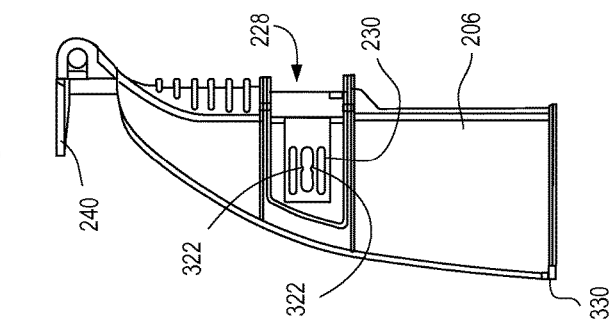
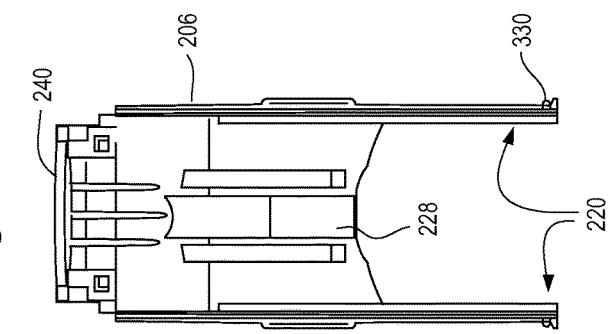

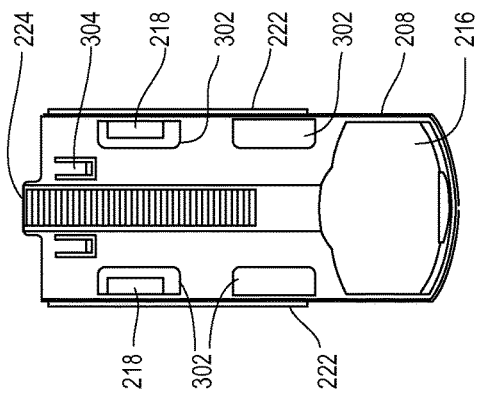
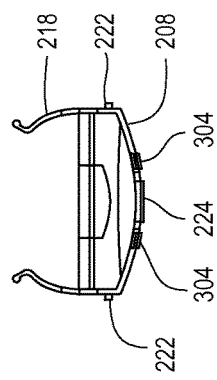
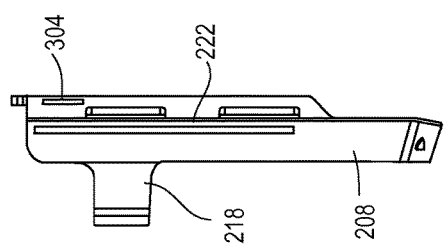
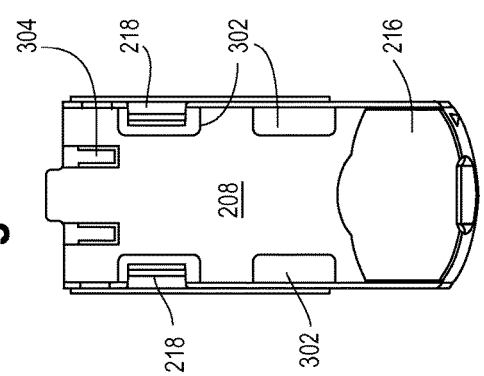

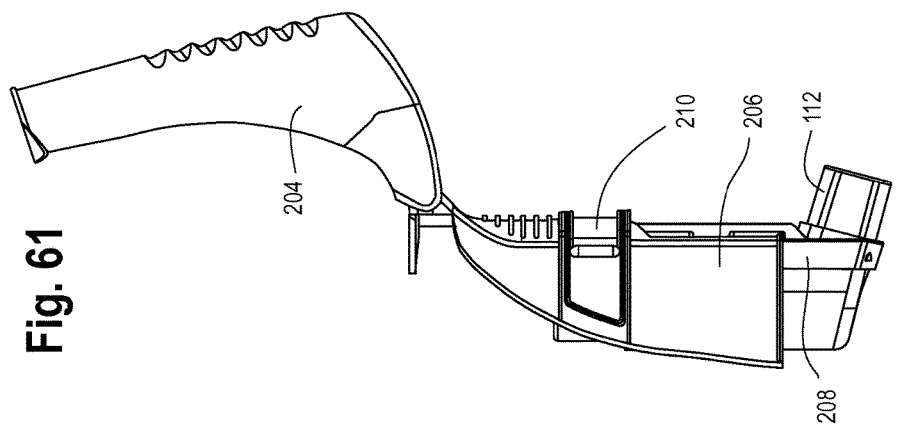
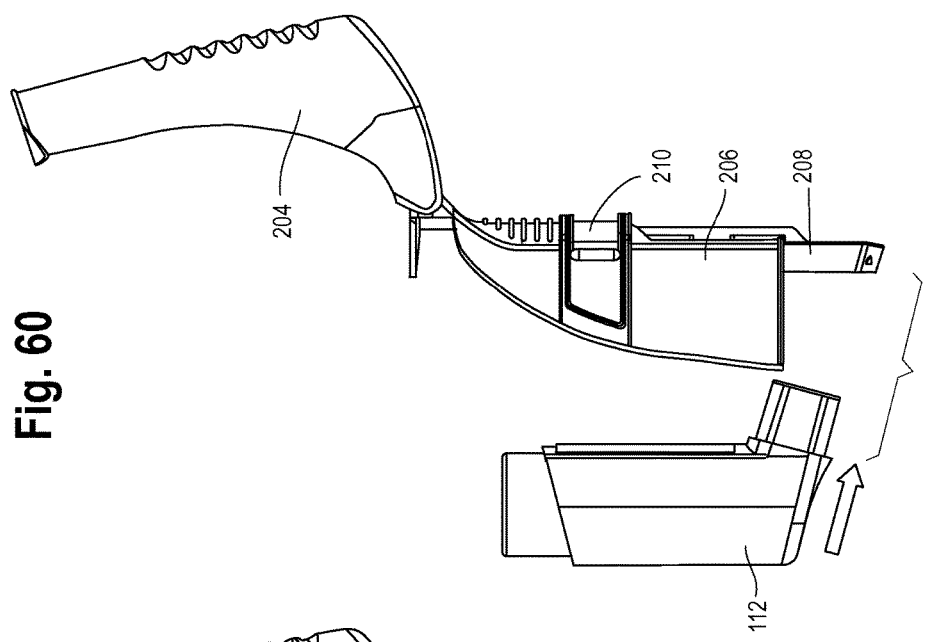
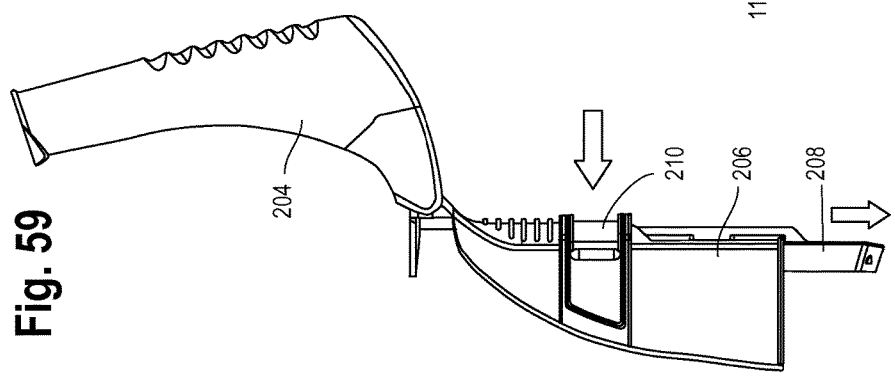

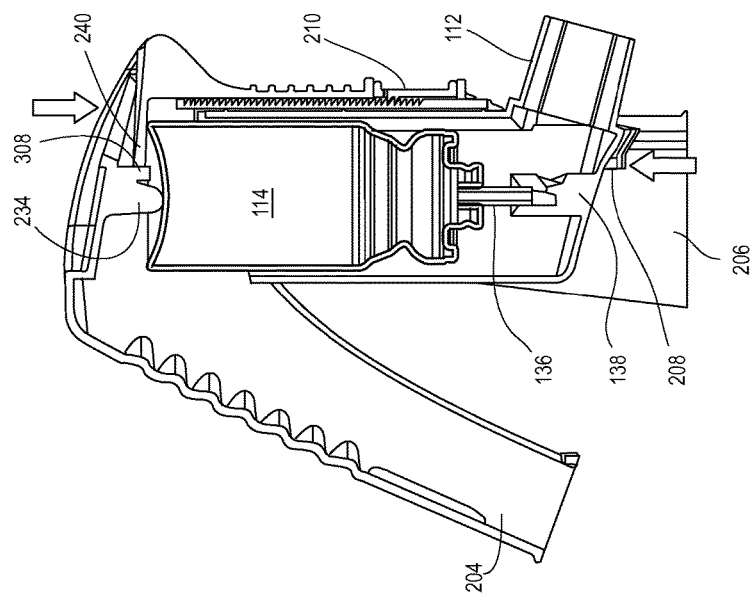

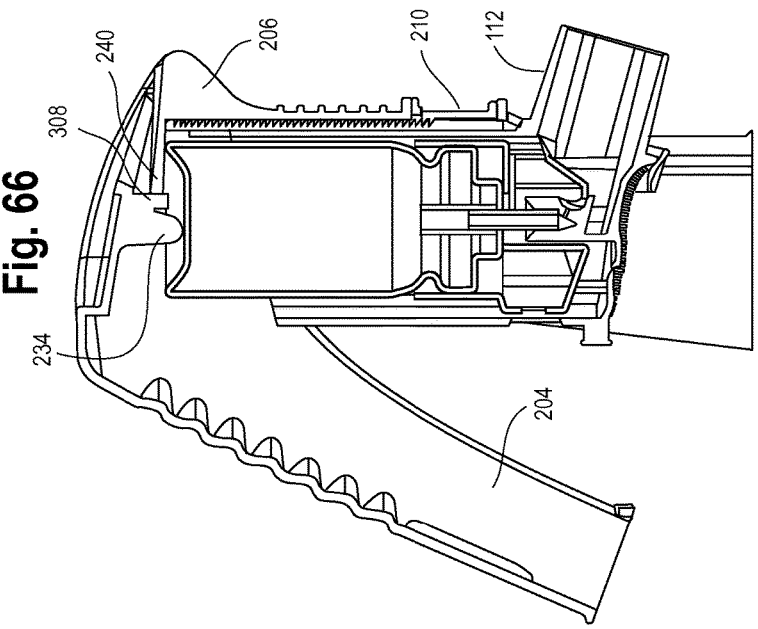
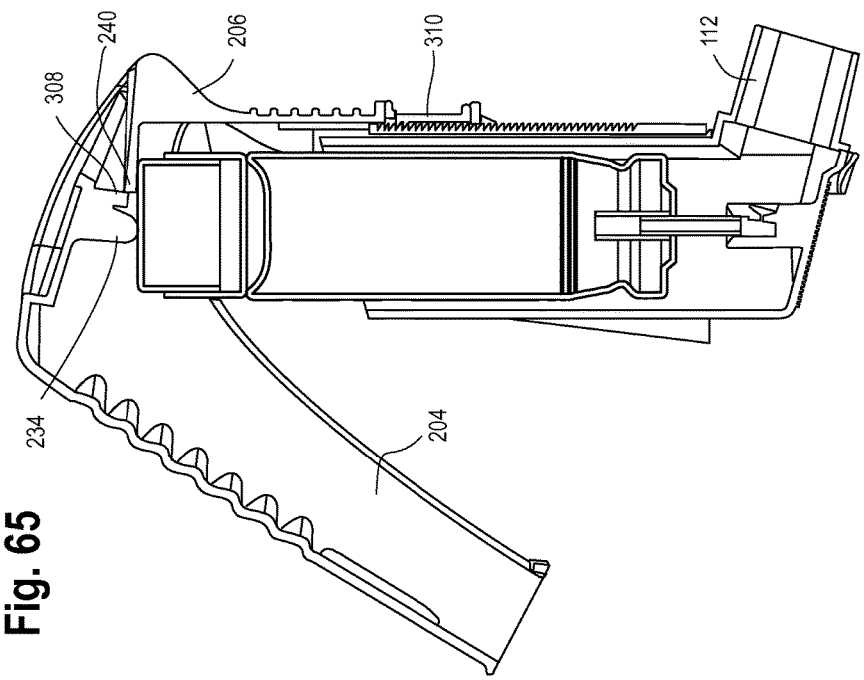

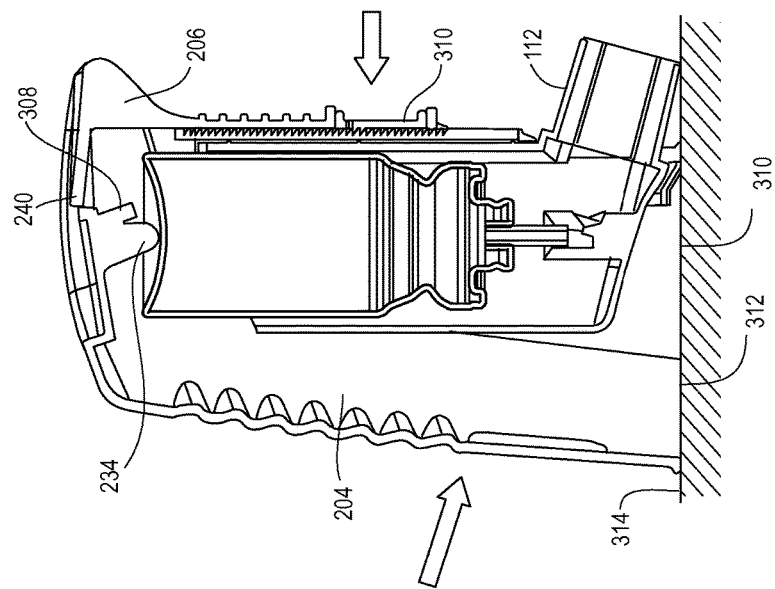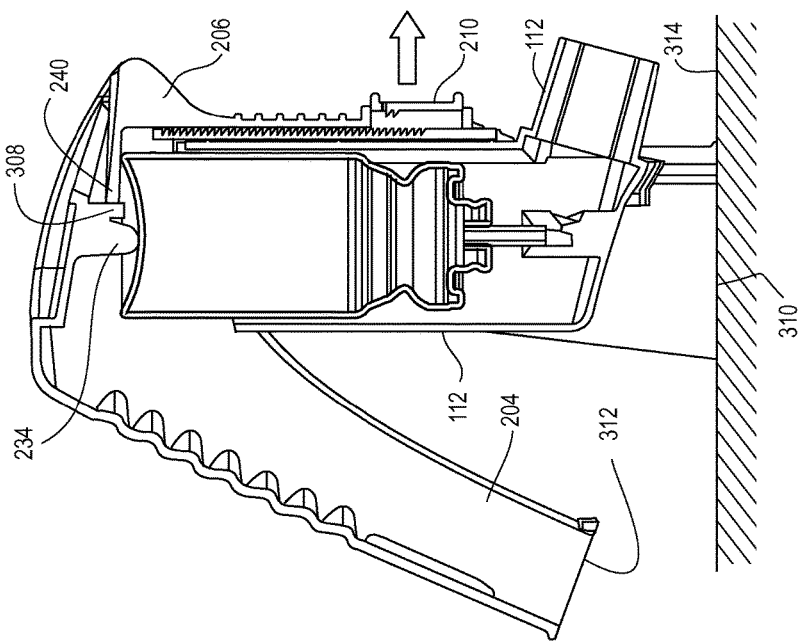

US 10,143,812 B2

METERED DOSE INHALER APPLICATOR

This application is a continuation of International Application PCT/IB2014/000291, filed Mar. 11, 2014, which claims the benefit of U.S. Provisional Application No. 61/781,828, filed Mar. 14, 2013, the entire disclosures of which is hereby incorporated herein by reference.

BACKGROUND

Metered dose inhalers (MDI) are devices that produce aerosolized medicines. Physicians generally use a MDI to deliver a specific amount of medicine to the lungs of a patient. The MDI produces a burst of aerosolized medicine, which the patient then inhales.

A MDI typically includes a canister, a metering valve, and an actuator. The canister holds a pressurized medicine, the metering valve restricts an amount of medicine that is dispensed when the MDI is actuated, and the actuator, that typically includes a stem and nozzle communication with the metering valve, provide the ability to dispense a limited amount of medicine from the canister and metering valve in an aerosolized from.

Patients may have difficulty actuating a MDI or storing a MDI in a manner that prevents inadvertent actuations. Accordingly, improved applicators for use with a MDI that provide the ability to easily actuate the MDI and that provide for convenient storage of the MDI are desirable.

BRIEF DESCRIPTION OF THE DRAWINGS

FIG. 2 is a side view of one implementation of a MDI applicator.

FIG. 3 is a rear view the MDI applicator of FIG. 2.

FIG. 4 is a top view of the MDI applicator of FIG. 2.

FIG. 5 is a front view of the MDI applicator of FIG. 2.

FIG. 6 is a cross-sectional view of the MDI applicator taken along line 6-6 of FIG. 5.

FIG. 7 is an exploded view of the MDI applicator of FIG. 2.

FIG. 8 is a front view of a lever of the MDI applicator of FIG. 2.

FIG. 9 is a side view of the lever of the MDI applicator of FIG. 2.

FIG. 10 is a rear view of the lever of the MDI applicator of FIG. 2.

FIG. 11 is a top view of the lever of the MDI applicator of FIG. 2.

FIG. 16 is a front view of a carrier of the MDI applicator of FIG. 2.

FIG. 17 is a side view of the carrier of the MDI applicator of FIG. 2.

FIG. 18 is a rear view of the carrier of the MDI applicator of FIG. 2.

FIG. 19 is a top view of the carrier of the MDI applicator of FIG. 2.

FIGS. 24-35 are drawings illustrating a procedure for positioning a metered dose inhaler in the MDI applicator of FIG. 2 and utilizing the MDI applicator to dispense aerosolized medicine.

FIGS. 36 and 37 are drawings illustrating a procedure for placing a MDI applicator in a storage configuration.

FIGS. 38 and 39 are drawing illustrating another implementation of a MDI applicator with a pivoting adjuster.

FIGS. 44-49 illustrate additional implementations of a MDI applicator.

FIG. 51A is a top view of another implementation of a MDI applicator.

FIG. 51 B is a side view of the MDI applicator shown in FIG. 51A.

FIG. 51C is a rear view of the MDI applicator shown in FIG. 51A.

FIG. 51D is a front view of the MDI applicator shown in FIG. 51A.

FIG. 51E is a cross-sectional view of the MDI applicator taken along line 51E-51E of FIG. 51D.

FIGS. 53A-D are top, rear, side and front views of the lever of the MDI applicator shown in FIG. 51A.

FIGS. 54A-D are top, rear, side and front views of the housing of the MDI applicator shown in FIG. 51A.

FIGS. 55A-D are top, rear, side and front views of the carrier of the MDI applicator shown in FIG. 51A.

FIGS. 57-66 are drawings illustrating a procedure for positioning a metered dose inhaler in the MDI applicator of FIG. 2 and utilizing, the MDI applicator to dispense aerosolized medicine.

FIGS. 67 and 68 are drawings illustrating a procedure for placing a MEN applicator in a storage configuration.

DETAILED DESCRIPTION OF THE DRAWINGS

Figure 1:
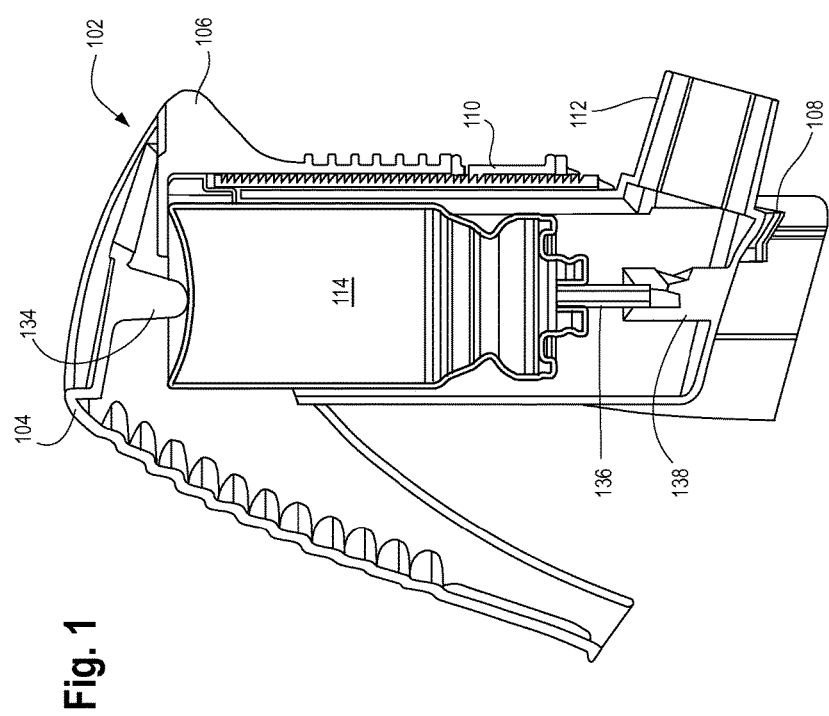
FIG. 1 is cross-sectional view of one implementation of a metered dose inhaler (MDI) positioned in a MDI applicator.
Figure 14:
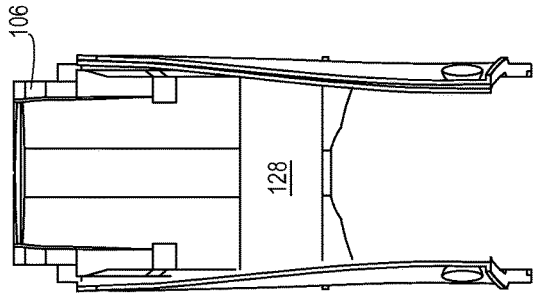
FIG. 14 is a rear view of the housing of the MDI applicator of FIG. 2.
Figure 13:
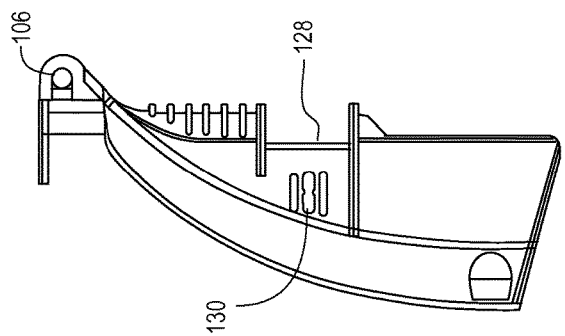
FIG. 13 is a side view of the housing of the MDI applicator of FIG. 2.
Figure 12:
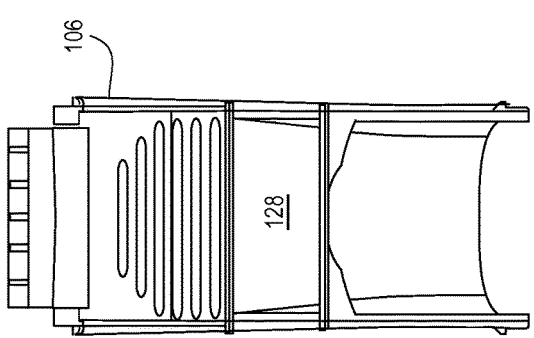
FIG. 12 is a front view of a housing of the MDI applicator of FIG. 2.
Figure 15:
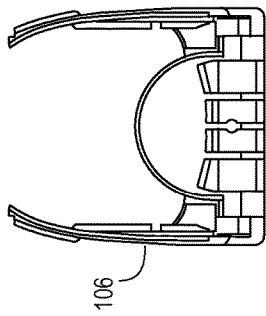
FIG. 15 is a top view of the housing of the MDI applicator of FIG. 2.
Figure 20:
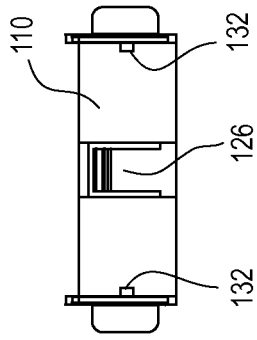
FIG. 20 is a front view of an adjuster of the MDI applicator of FIG. 2.
Figure 21:
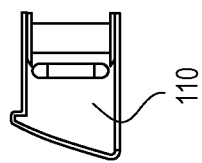
FIG. 21 is a side view of the adjuster of the MDI applicator of FIG. 2.
Figure 22:
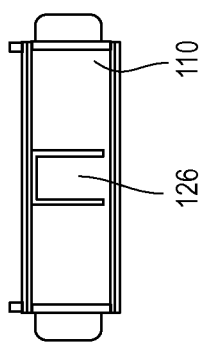
FIG. 22 is a rear view of the adjuster of the MDI applicator of FIG. 2
Figure 23:
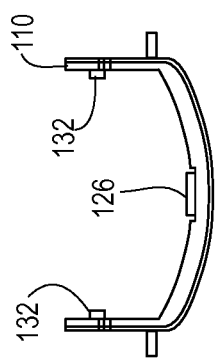
FIG. 23 is a top view of the adjuster of the MDI applicator of FIG. 2.

The present disclosure is directed to a metered dose inhaler (MDI) applicator that provides a lever to assist a patient in actuating a MDI. FIG. 1 is a cross-sectional view of one implementation of a MDI 112 positioned in a MDI applicator 102. The MDI applicator 102 may include a lever 104, a housing 106, a carrier 108, and an adjuster 110.

As explained in more detail below, the lever 104 is positioned on the MDI applicator 102 such that when a force is applied to the lever 104 of the MDI applicator 102, the lever 104 transfers the force to a canister 114 of the MDI 112 positioned in the MDI applicator 102. When sufficient force is applied to the canister 114 of the MDI 112 via the lever 104, the MDI 112 dispenses an aerosolized medicine that a patient may inhale.

FIGS. 3-6 and 51A-52 illustrate various views of the MDI applicator 102, 202; FIG. 7 illustrates an exploded view of the MDI applicator 102, 202; FIGS. 8-11 and 53A-D illustrate various views of the lever 104, 204 of the MDI applicator 102; FIGS. 12-15 and 54A-D illustrate various views of the housing 106, 206 of the MDI applicator 102; FIGS. 16-49 and 55A-D illustrate various views of the carrier 108, 208 of the MDI applicator 102; and FIGS. 20-23 and 56A-D illustrate various views of the adjuster 110, 210 of the MDI applicator 102.

Figure 52:
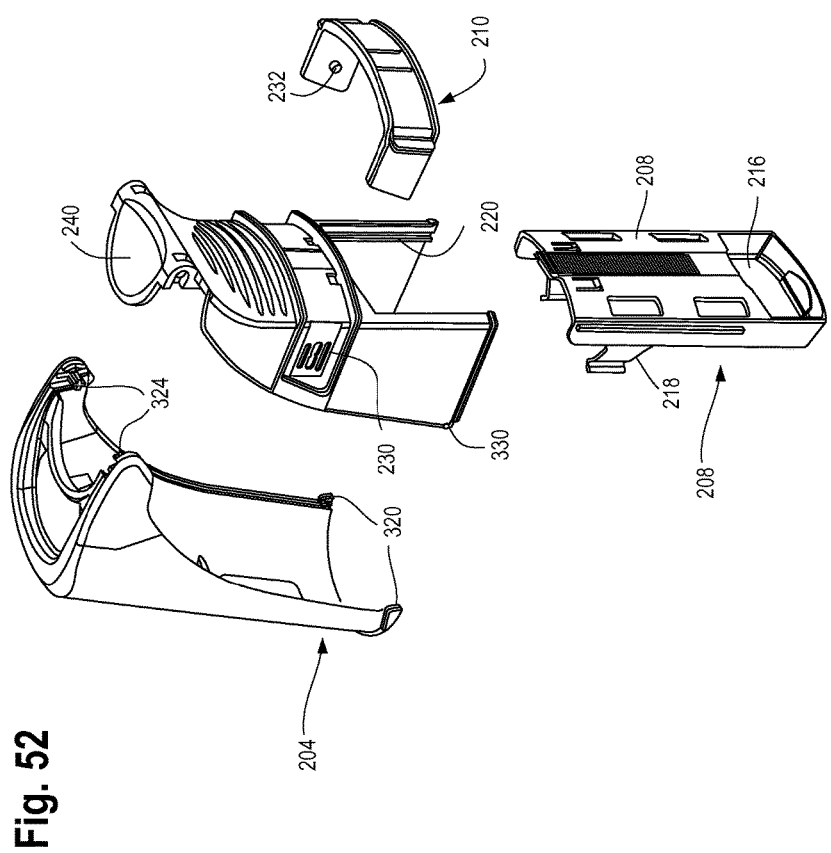
FIG. 52 is an exploded view of the MDI applicator shown in FIG. 51A.
Figure 56D:
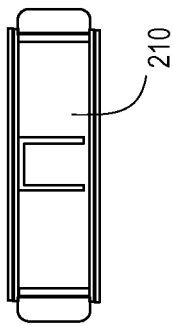
FIGS. 56A-D are top, rear, side and front views of the adjuster of the MDI applicator shown in FIG. 51A.
Figure 56C:
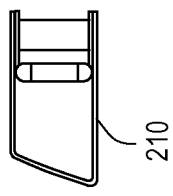
Figure 56B:
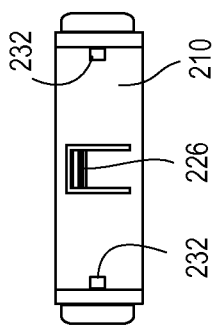
Figure 56A:
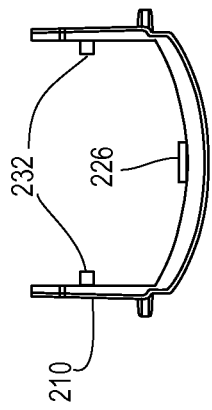

Referring to FIGS. 7 and 52, the carrier 108, 208 defines an aperture 116, 216 that is dimensioned to receive a boot of a MDI. When the carrier 108, 208 receives the boot of the MDI, the boot of the MDI passes through the carrier 108, 208 in a telescopic manner. In some implementations, the carrier 108, 208 may include one or more prongs 118, 218 positioned on either side of the carrier 108, 218. The prongs 118, 218 are configured to engage with the MDI and to secure the earlier 108, 208, and the MDI applicator 102, 202 as a whole, to the MDI. As shown in FIGS. 55A-D, a plurality of openings are formed in the face of the carrier, with two of the openings underlying the prongs 218, thereby facilitating the molding process. In addition, a pair of limit stop hooks 304 are formed in the face on opposite sides of the rack of teeth 224. The hooks 304 are flexible. When assembling the carrier 108, 208 to the housing 106, 206, the hooks 304 deflect as the guide tabs 122, 222 of the carrier 108, 208 slides on guide channels 120, 220 into the housing 106, 206. When the hooks 304 pass over the ledge 140, 240, as shown in. FIG. 54A, of the two small square openings on either side of 228, they allow the carrier 08, 208 to slide all the way into the housing 106, 206 in the upward direction, but stop the carrier 108, 208 in the downward direction when the hooks 304 engage the ledge 140, 240.

The housing 106, 206 and the carrier 108, 208 are configured to be assembled to one another in the MDI applicator 102. In some implementations, the housing 106, 206 and the carrier 108, 208 are configured to move in relation to one another in a vertical manner so that the MDI applicator 102, 202 may accommodate MDIs of various heights.

To assist in the relative movement between the housing 106, 206 and the carrier 108, 208, in some implementations the housing 106, 206 may define one or more guide channels 120 and the carrier 108, 208 may define one or more guide tabs 122, 222. When the housing 106, 206 and the carrier 108, 208 are assembled, the guide tabs 122, 222 of the carrier 108, 208 are positioned in the guide channels 120, 220 of the housing 106, 206 to restrict movement between the housing 106, 206 and the carrier 108, 208 to vertical movement.

As will be explained in more detail below, when a MDI is positioned within the MDI applicator 102, 202, the housing 106, 206 and the carrier 108, 208 are adjusted in a vertical manner to accommodate the height of the MDI. After the housing 106, 206 and the carrier 108, 208 are adjusted to the proper height, the adjuster 110, 210 locks the position of the housing 106, 206 relative to the carrier 108 to prevent further movement.

In some implementations, the carrier 108, 208 defines a set of teeth 124, 224, or rack, and the adjuster 110, 210 defines a complementary set of teeth 126, 226. The teeth of the adjuster may be configured as a single tooth. The teeth 226 may be formed on a resilient tab. Further, the housing 106, 206 defines an aperture 128, 228 such that as the housing 106, 206 and the carrier 108, 208 move relative to each other, at least a portion of the set of teeth 124, 224 defined by the carrier 108, 208 is exposed. Referring to FIGS. 51B-E, 67 and 68, the bottom of the housing, and the bottom of the lever are each configured with a flat bottom edge 310 and 312, allowing the applicator 202, with or without a MDI 112, to stand upright on a flat surface 314.

The adjuster 110, 210 is positioned on housing 106, 206 and is configured to move between a locked position and an unlocked position. In some implementations, when the adjuster 110, 210 is in the locked position, the teeth 126, 226 of the adjuster 110, 210 engage the portion of the teeth 124, 224 of the carrier 108, 208 positioned in the aperture 128, 228 of the housing 106, 206. When the complementary sets of teeth 124, 224 and 126, 226 engage, the engaged teeth restrict the vertical movement between the housing 106, 206 and the carrier 108, 208. In some implementations, the engaged teeth 124, 224 and 126, 226 are shaped to restrict movement in all directions such that the vertical height of the MDI applicator 102, 202 may not be reduced or increased. However, in other implementations, the engaged teeth are shaped and configured only to restrict movement in a direction such that the height of MDI applicator 102, 202 may be reduced, but not increased.

In some implementations, the adjuster 110, 220 may move in a horizontal direction relative to the housing 106, 206 to move from the locked position to the unlocked position. It will be appreciated that to move the adjuster 110, 210 into the unlocked position, the adjuster 110, 210 is moved away from the housing 106, 206. Moving the adjuster 110, 210 away from the housing 106, 206 moves the teeth 126, 226 of the adjuster 110, 210 away from the teeth 124, 224 of the carrier 108, 208 that are positioned in the aperture 128, 228 of the housing 106, 206. Because the teeth 124, 224 of the carrier 108, 206 are no longer engaged with the teeth 126, 226 of the adjuster 110, 210, the housing 106, 206 and the carrier 108, 208 are free to move in a vertical direction relative to each other.

In some implementations, to assist the adjuster 110, 210 in moving in a horizontal direction relative to the housing 106, 206, the housing may define one or more guide channels 130, 230 and the adjuster 110, 210 may define one or more guide posts 132, 232. When the housing 106, 206 and the adjuster 110, 210 are assembled, the guide posts 132, 232 of the adjuster 110, 210 are positioned within the one or more guide channels 130, 230 of the housing 106, 206 to restrict movement of the adjuster 110, 210 with respect to the housing 106, 206 to a horizontal direction. Detents 322 are located along the sides of the guide channels to hold the adjuster in the locked position, with the adjuster teeth 126, 226 in engagement with the teeth. 124, 224 of the carrier. In one embodiment, the carrier may be moved upwardly relative to the housing as the teeth 126, 226 ratchet past the teeth 124, 224, but does not allow downward movement, since the adjuster rests on the housing lower ledge. When the adjuster 110, 210 is moved past the housing detents 322 to the unlocked position, the adjuster teeth 126, 226 disengage from the teeth 124, 224 on the carrier. This allows upward or downward motion of the carrier relative to the housing to install a MDI or to set to the storage position.

The lever 104, 204 is pivotally connected to the housing 106, 206 at an end of the housing 106, 206, for example with a pair of posts 324, such that a user may place a force on the lever to cause the lever to move towards the housing 106, 206. In one implementation, the lever defines a post 134, 234 on an underside of the lever. However, in other implementations, the lever may define a protrusion having a shape other than a post. The lever may be configured with detents 320, which engage protuberances 330 on the sides of the housing when closed. Detents 320 engage the protuberances 330 to form a closure detent.

Referring to FIGS. 1 and 62, when the MDI 112 is positioned within the MDI applicator 102, 202, the post 134, 234 of the lever 104 is positioned against an end of the canister 114 of the MDI 112. Generally, when a force is applied to the lever 104, 204 of the MDI applicator 102, 202 the pivotal movement of the lever 104, 204 and the post 134, 234 transfers the force applied to the lever 104, 204 to a downward force against the canister 114 of the MDI 112. When the downward force against the canister 114 of the MDI 112 causes a stem 136, 236 of the MDI 112 to compress enough to open an internal valve of the MDI 112, medicine within the canister passes through the stem 136 and out of a nozzle 138 of the MDI 112 in an aerosolized form for inhalation by a patient.

Figure 24:
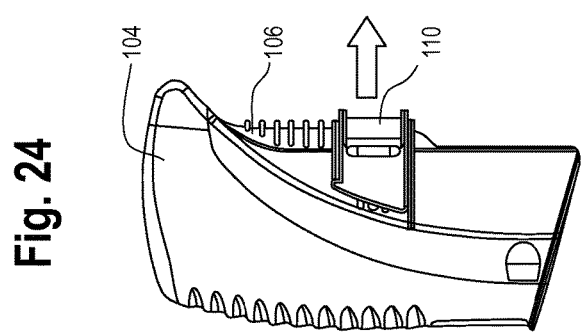
Figure 57:
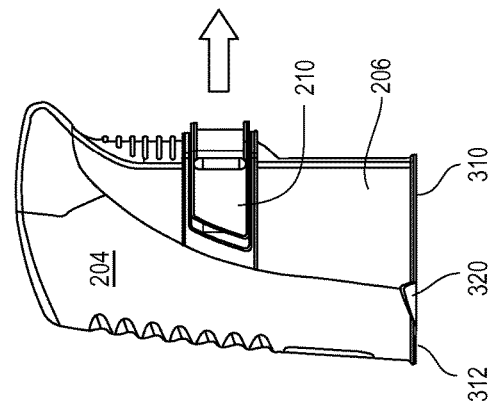
Figure 63:
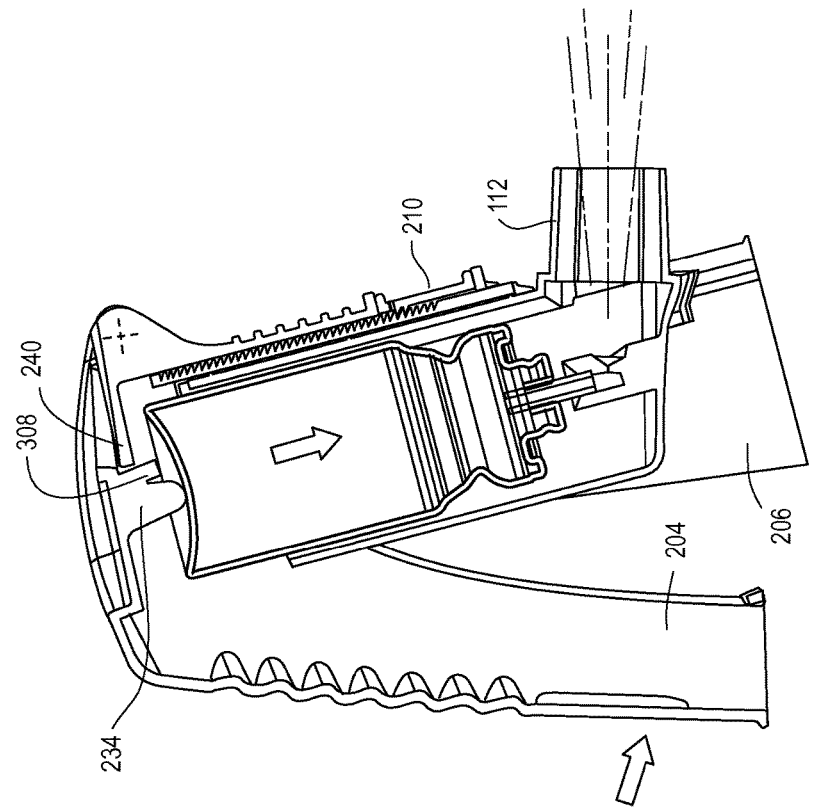
Figure 64:
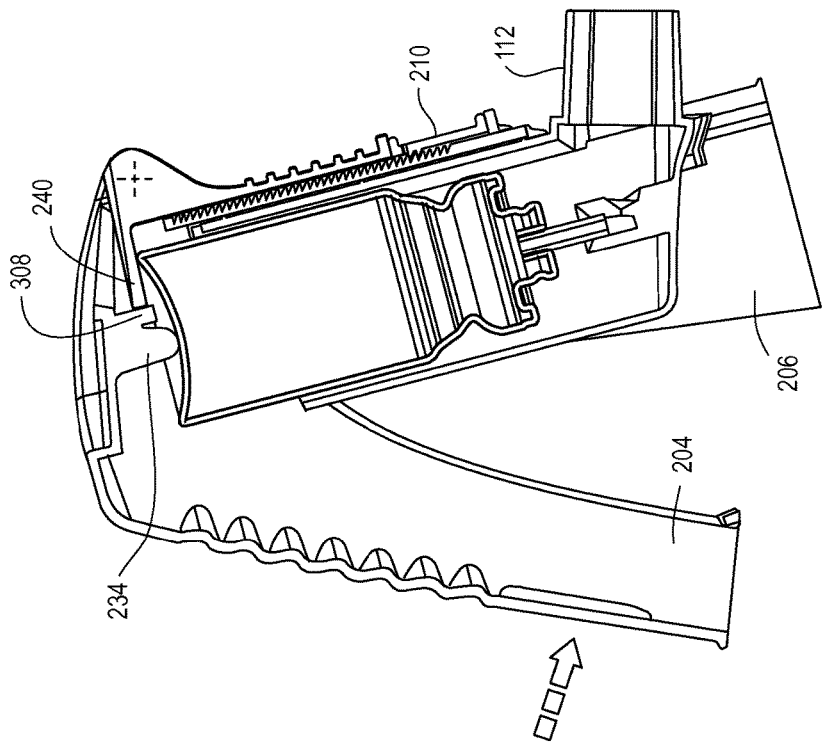

FIGS. 24-35 and 57-66 are drawings illustrating a procedure for positioning a metered dose inhaler in the MDI applicator and utilizing the MDI applicator to dispense aerosolized medicine. As shown in FIGS. 24 and 57, the adjuster 110, 210 is moved away from the housing 106, 206 and into an unlocked position. As discussed above, moving the adjuster 110, 210 into the unlocked position allows the housing 106, 206 and the carrier 108, 208 to move in a vertical direction relative to one another in order to accommodate MDI's of various sizes.

Figure 25:
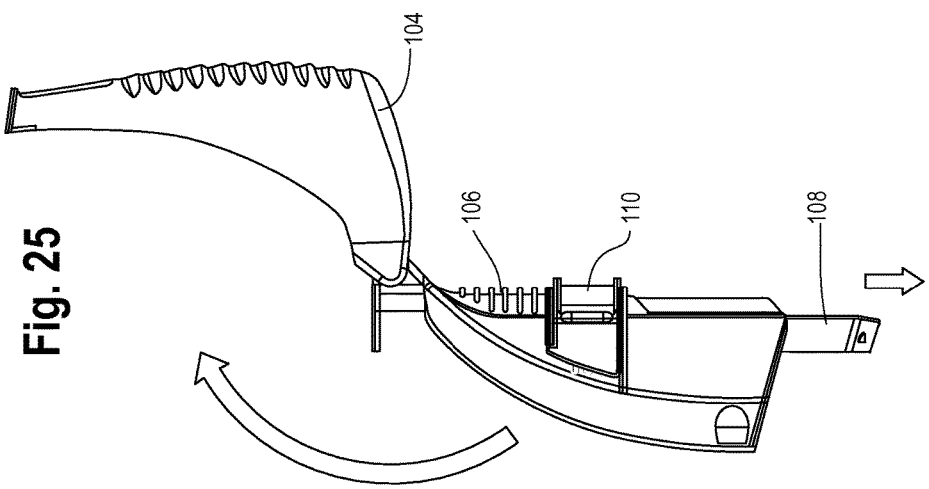
Figure 58:
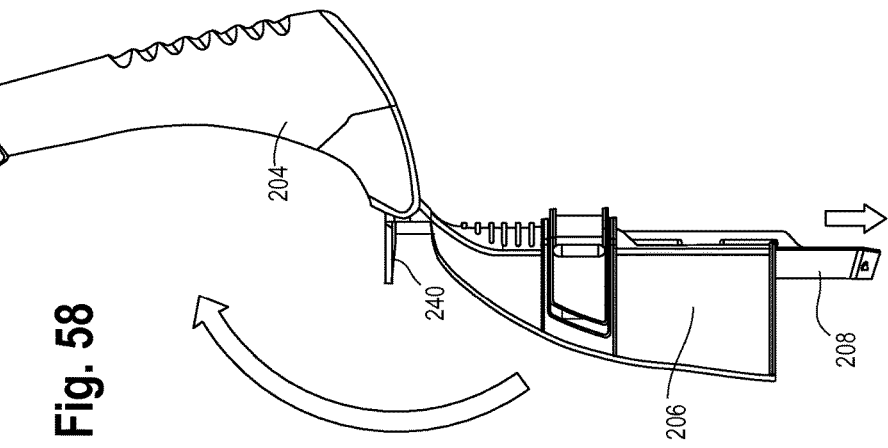

As shown in FIGS. 25 and 58, the carrier 108 is pulled down relative to the housing 106, 206. In some implementations the housing 106, 206 and the carrier 108, 208 may include one or more stops in order to prevent the housing and 106, 206 and the carrier 108, 208 from separating. The lever 104, 204 is additionally pivoted to an open position so that the MDI applicator 102, 202 is configured to receive the MDI 112.

As shown in FIGS. 26 and 59, once the carrier 108, 208 is pulled down relative to the housing 106, 206, the adjuster 110, 210 is moved towards the housing 106, 206 and into the locked position. As discussed above, moving the adjuster 110, 210 into the locked position restricts movement between the housing 106, 206 and the carrier 108, 208 in one or more directions.

Figure 29:
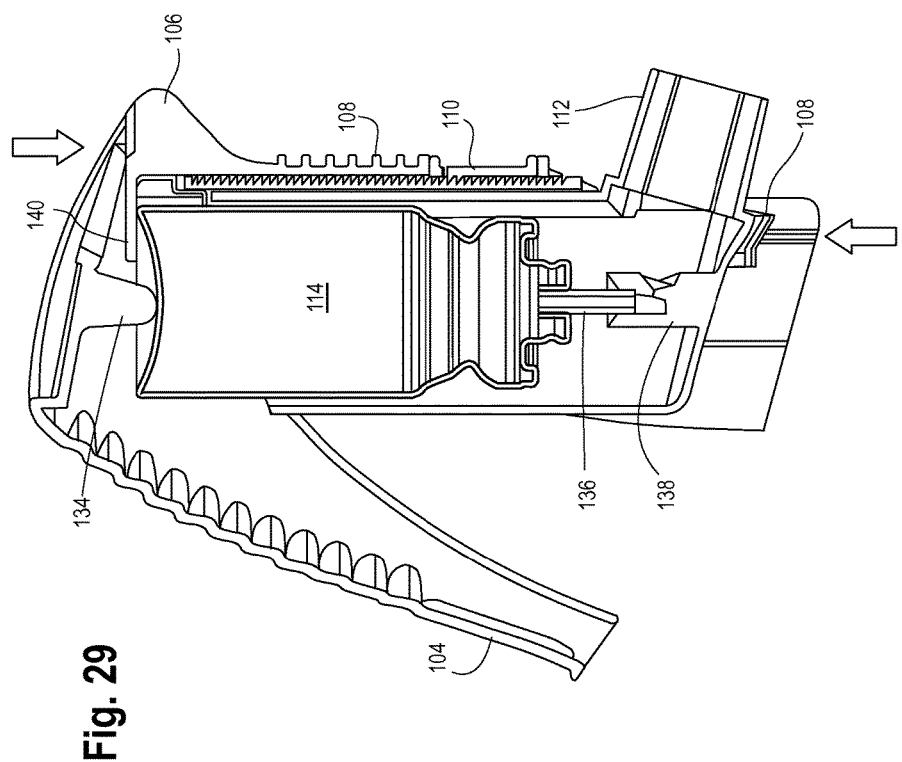
Figure 31:
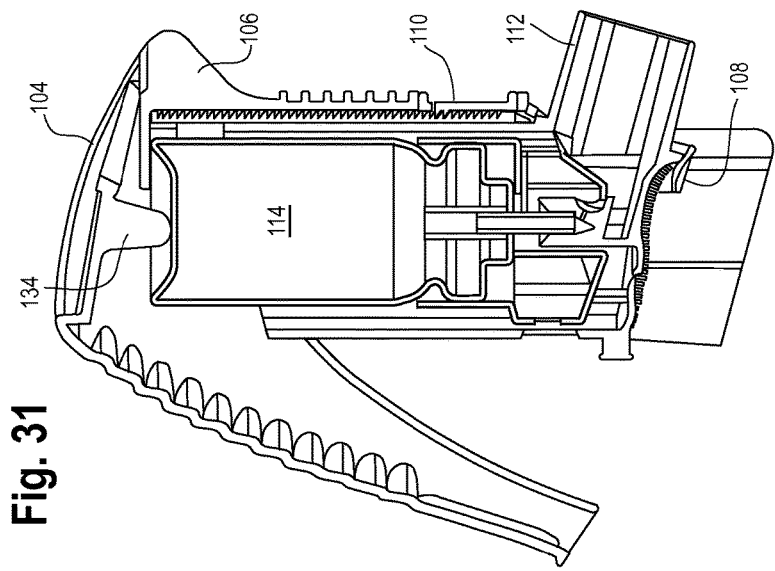
Figure 30:
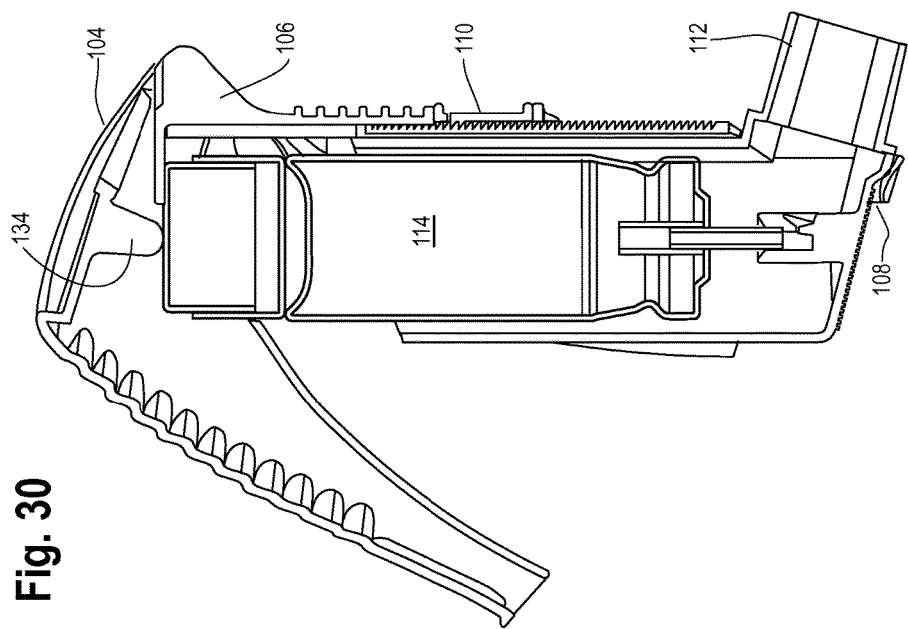
Figure 32:
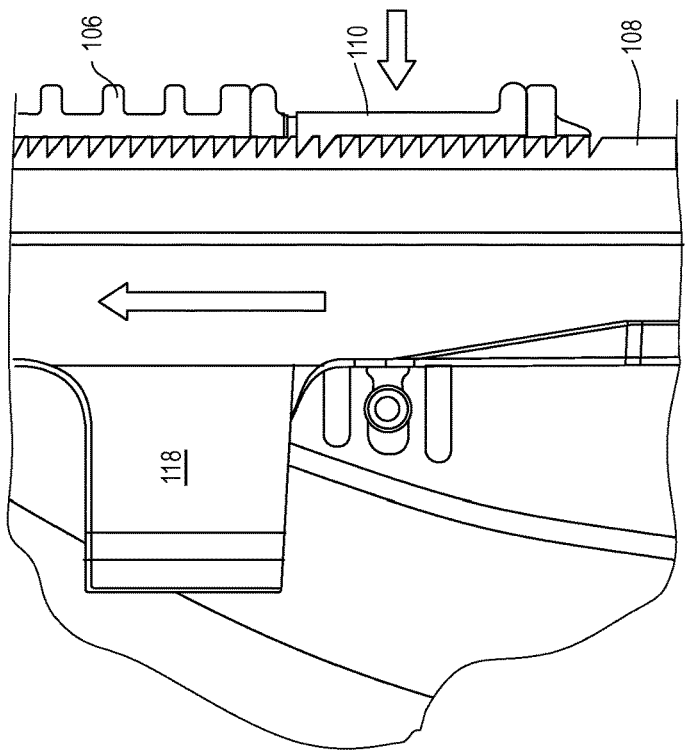
Figure 33:
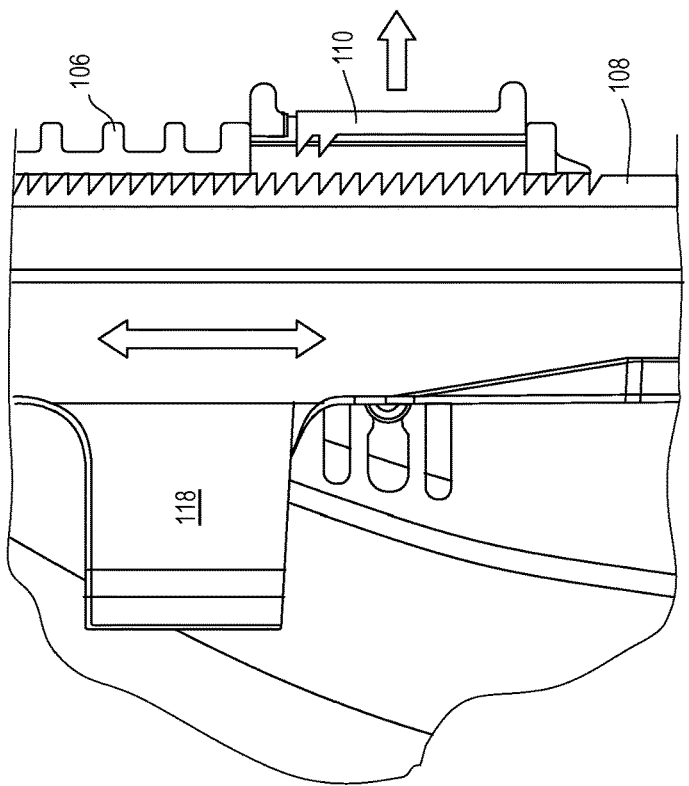
Figure 35:
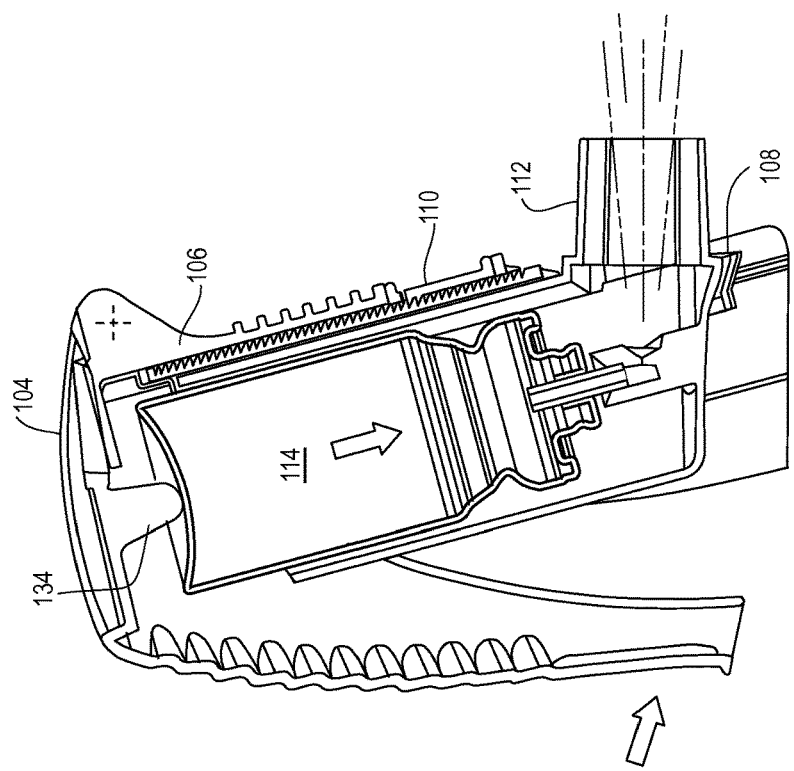
Figure 34:
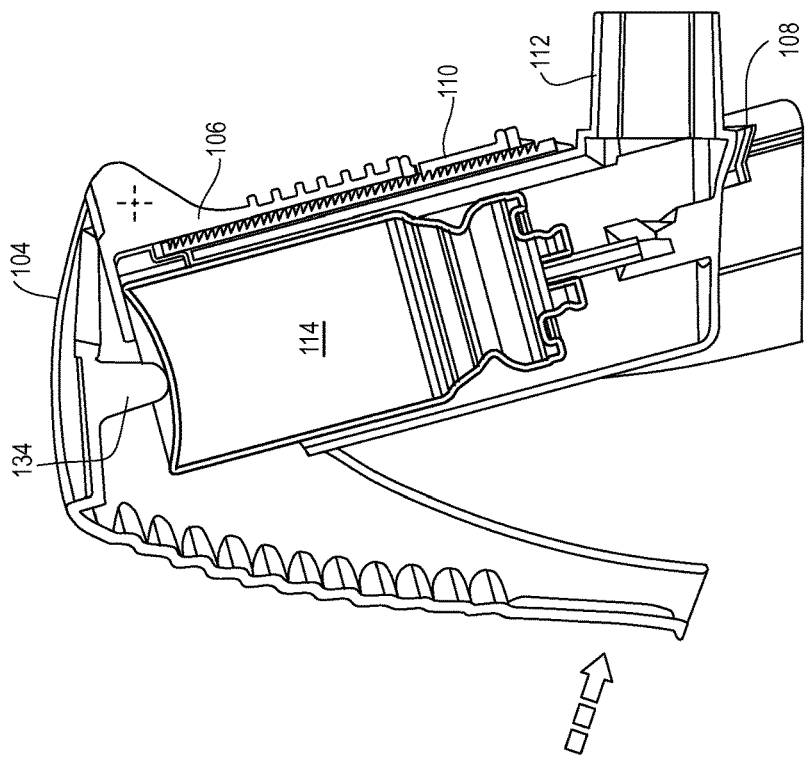

As shown in FIGS. 27, 28, 60 and 61, the MDI 112 is inserted into the aperture 116, 216 of the carrier 108, 208. Once the boot of the MDI 112 is fully seated in the carrier 108, 208, the housing 106, 206 and the carrier 108, 208 are compressed as shown in FIGS. 29 and 62 to reduce the height of the MDI applicator 102, 202. In some implementations, the housing 06 and the carrier 108 are compressed until a ledge 140, 240 of the housing 106 comes in contact with the canister 114 of the MDI 112. Referring to FIG. 62, the lever includes a stop 308 that engages the top of the canister 114 when setting the correct height for the boot of the MDI 112.

It will be appreciated that the process of adjusting a distance between the housing 106, 206 and the carrier 108, 208 provides the MDI applicator 102, 202 the ability to accommodate MDI's of various heights, as shown in FIGS. 30, 31, 65 and 66. For example the applicator 202 may accommodate MDI's between 71.5 mm and 98 mm.

In some implementations, the distance between the housing 106, 206 and the carrier 108, 208 must be adjusted while the adjuster 110, 210 is in the unlocked position. However, in other implementations, such as those shown in FIGS. 32 and 33, a distance between the housing 106, 206 and the carrier 108, 208 may be adjusted while the adjuster 110, 2 0 is in the locked position. In these implementations, the teeth 124, 224 of the carrier 108, 208 and the complementary teeth 126, 226 of the adjuster 110, 210 are configured to allow a user to reduce the distance between the housing 106, 206 and the carrier 108, 208 while preventing the user from increasing the distance between the housing 106, 206 and the carrier 108, 208.

Referring to FIGS. 34, 35, 63 and 65, once the height of the MDI applicator 102, 202 is adjusted to properly accommodate the MDI 112, a user may apply a force to the lever 104, 204. Because the MDI 112 is securely positioned in the carrier 108, 208, as the lever 104, 204 pivotally moves towards the housing 106, 206 and the carrier 108, 208, the post 134, 234 of the lever 104, 204 applies a downward force on the canister 114 of the MDI 112. When the stem 136 of the MDI 112 is compressed enough to open an internal valve, a pressurized medication solution is released from the canister 114 through the stem 136. The medication solution is released into the nozzle 138 where it forms an aerosol plume as it enters the atmosphere.

When the MDI applicator 102, 202 is not in use, the MDI applicator 102, 202 may be moved into a storage position that prevents a user from inadvertently actuating the MDI 1 12. As shown in FIGS. 36, 37, 67 and 68, to move the MDI applicator 102, 202 into a storage position, the user first moves the adjuster 110, 210 into an unlocked position. Placing the adjuster 110, 210 in the unlocked position allows the housing 106, 206 and the carrier 108, 208 to move freely in a vertical direction with respect to one another.

After moving the adjuster 110, 210 into the unlocked position, the user may place a force on the lever 104, 204 to bring the lever against the housing 106, 206 as shown in FIG. 37. Because the housing 106, 206 and the carrier 108, 208 may move freely in a vertical direction with respect to one another, as the post 134, 234 of the lever 104, 204 presses against the canister 114 of the MDI 112, the force on the lever 104, 204 causes the housing 106, 206 to move away from the carrier 108, 208 and the height of the MDI applicator 102, 202 to increase. Further, it will be appreciated that because the force on the lever 104, 204 causes the housing 106, 206 to move away from the carrier 108, 208, the force on the lever 104, 204 does not additionally cause the stem 136 of the MDI 112 to compress. After moving the lever 104, 204 into a closed position, a user may then move the adjuster 110, 210 into the locked position to lock the lever 104, 204 against the housing 106, 206 and the carrier 108, 208.

FIGS. 38 and 39 illustrate another implementation of a MDI applicator 102. In the MDI applicator of FIGS. 38 and 39, the adjuster 110 is a pivot adjuster that may be pivoted between a locked and an unlocked position.

Figure 40A:
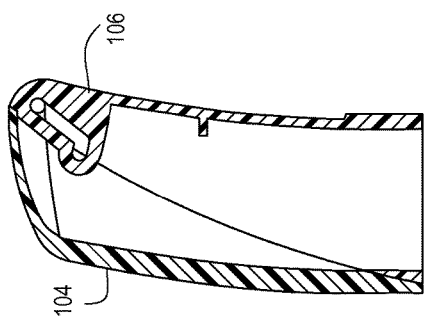
FIGS. 40A, 40B, 41A, and 41B are drawings illustrating a two-position lever of a MDI applicator.
Figure 40B:
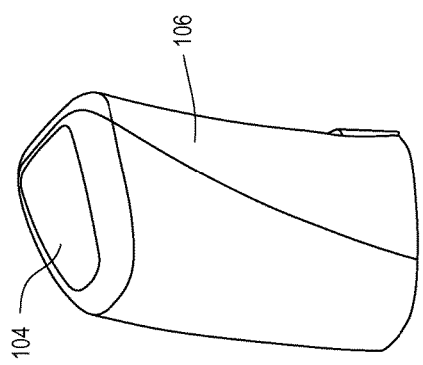
Figure 41A:
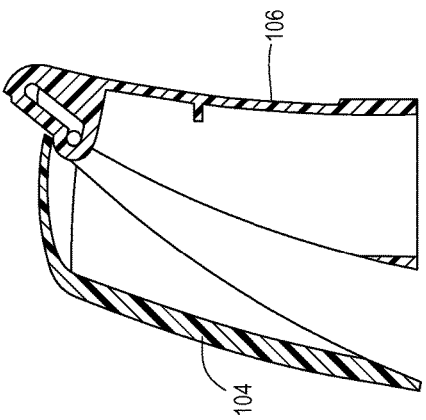
Figure 41B:
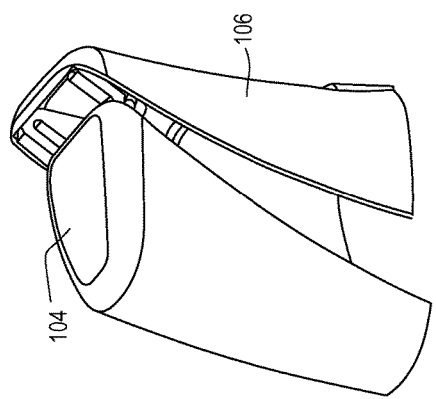

FIGS. 40A, 40B, 41A, and 41B are drawings illustrating a two-position lever 104 of a MDI applicator 102. As shown in FIGS. 40A and 40B the two-position lever 104 provides for the lever 104 to be in a first position when the MDI applicator 102 is in a closed position. However, when the MDI applicator 102 is in use, the lever 104 slides to a second position as shown in FIGS. 41A and 41B to provide more leverage in creating a downward force against the canister 114 of a MDI 112. It will be appreciated that a MDI applicator 102 with a two-position lever 104 may provide for a more compact MDI applicator 102 when not in use.

Figure 42:
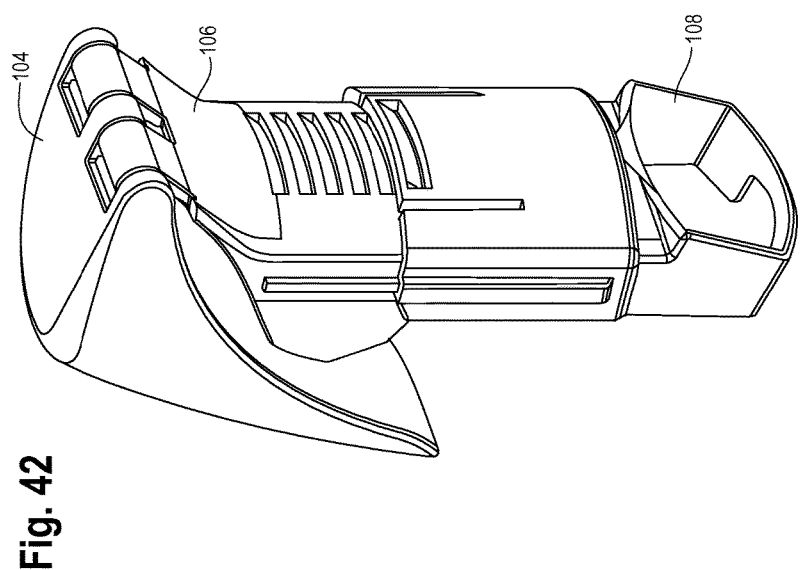
FIG. 42 is an illustration of another implementation of a MDI applicator.

FIG. 42 is an illustration of another implementation of a MD applicator 102. In this implementation, the MDI applicator 102 does not include an adjuster 110 that may be moved between a locked and an unlocked position. Instead, the housing 106 and the carrier 108 are in telescopic communication with each other such that the housing 106 and the carrier 108 may be locked into discrete positions.

Figure 43:
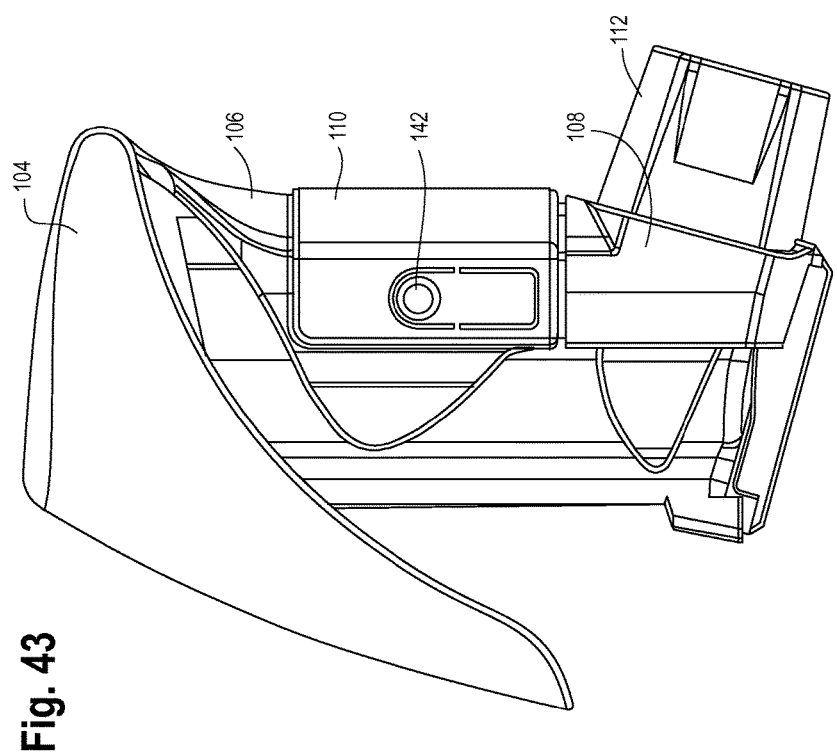
FIG. 43 is an illustration of yet another implementation of a MDI applicator.
Figure 44:
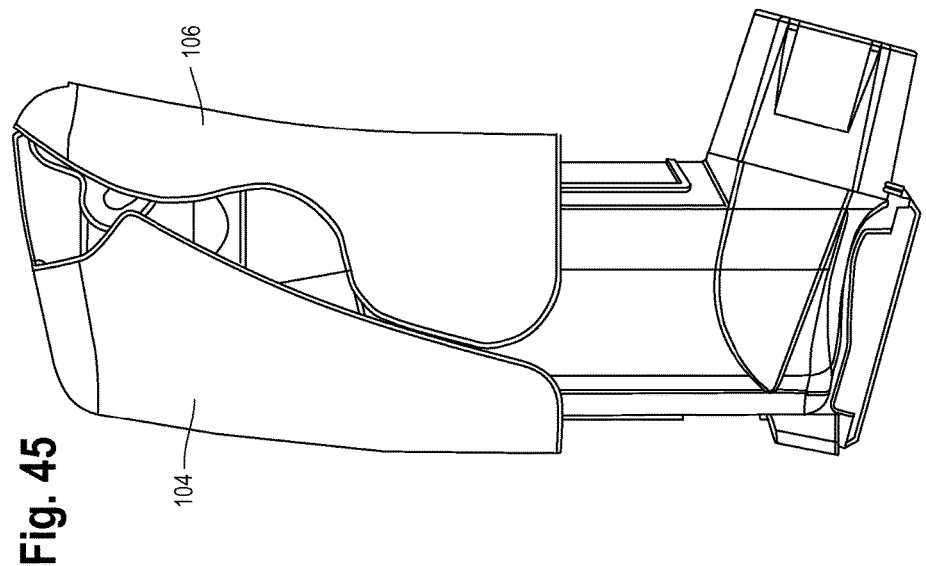
Figure 45:
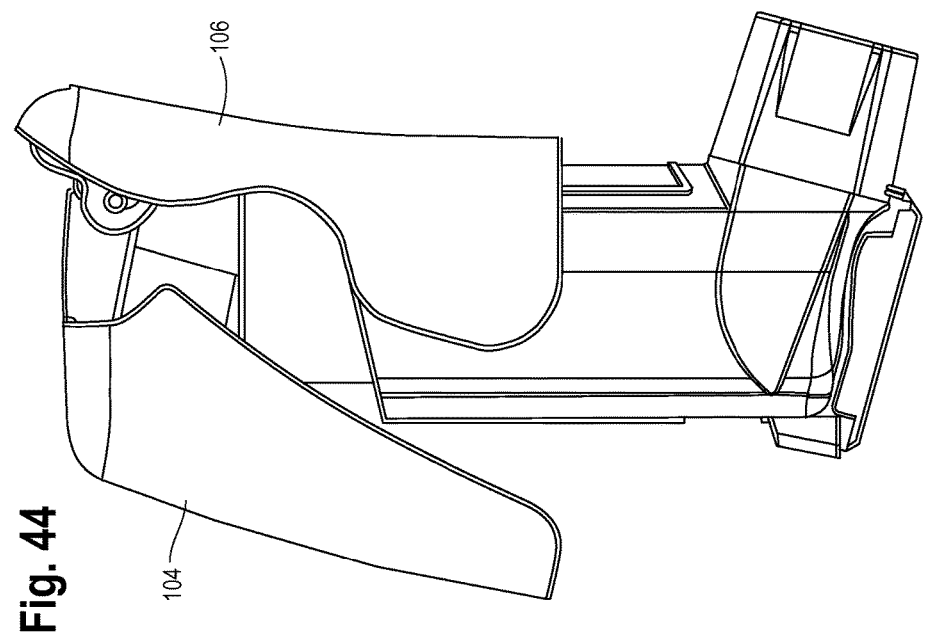
Figure 46:
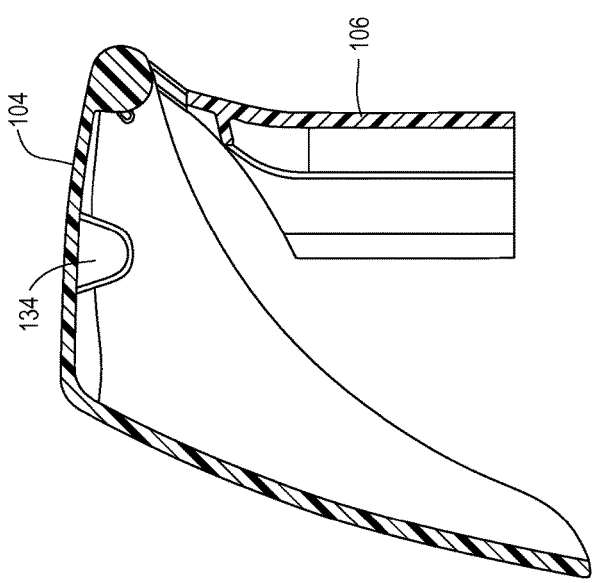
Figure 47:
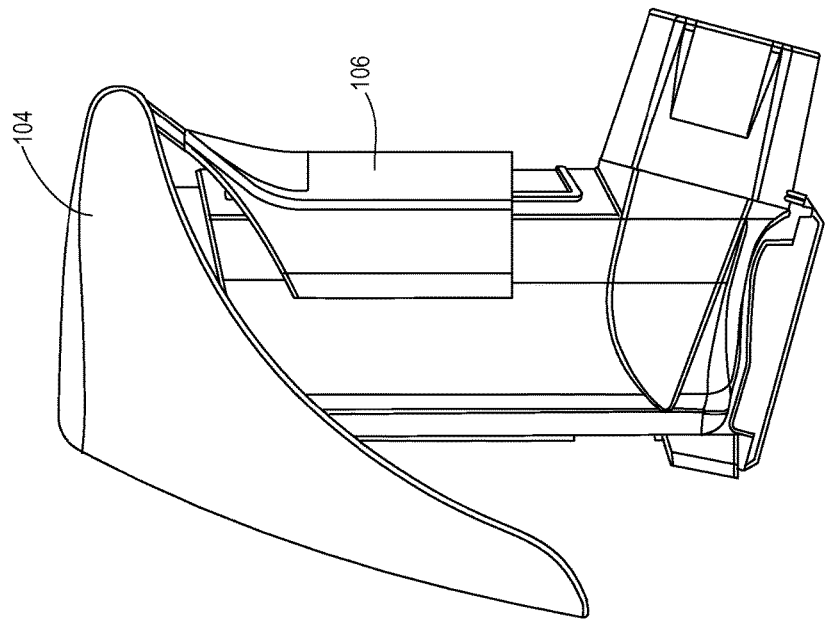

FIG. 43 is an illustration of yet another implementation of a MDI applicator. In the illustrated implementations, the adjuster 110 is an adjustment rack that may be moved between a locked and an unlocked position by means of side spring levers 142.

FIGS. 44-49 illustrate further implementations of a MDI applicator 102. In the illustrated implementations, the MDI applicator 102 does not include a carrier 108 and an adjuster 110. Instead, the housing 106 is secured to a boot of a MDI 112 through the use of an adhesive such as double-sided tape or a hook and loop attachment system. The lever 104 is pivotally connected to the housing 106 as described above.

Figure 50C:
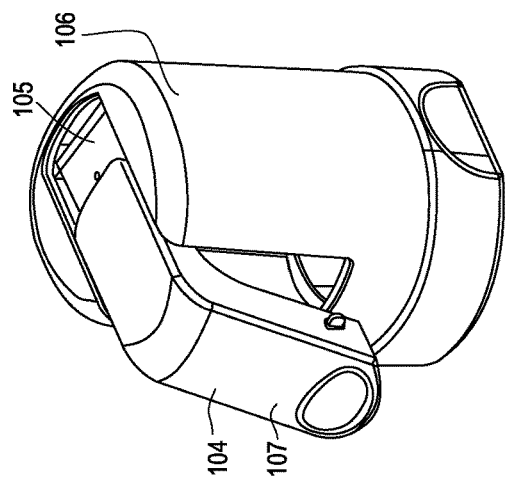
FIGS. 50A, 50B and 50C illustrate another implementation of a MDI applicator.
Figure 50B:
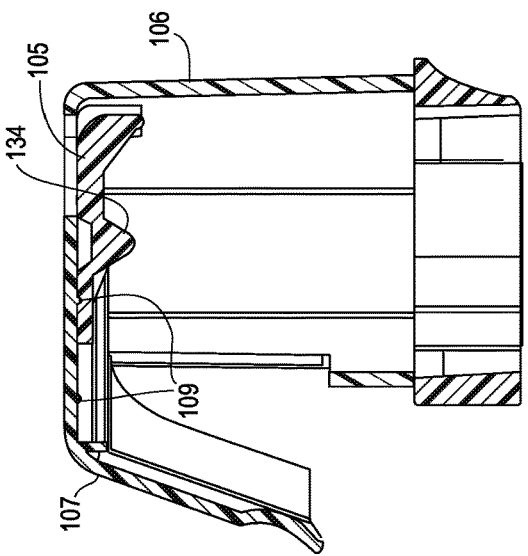
Figure 50A:
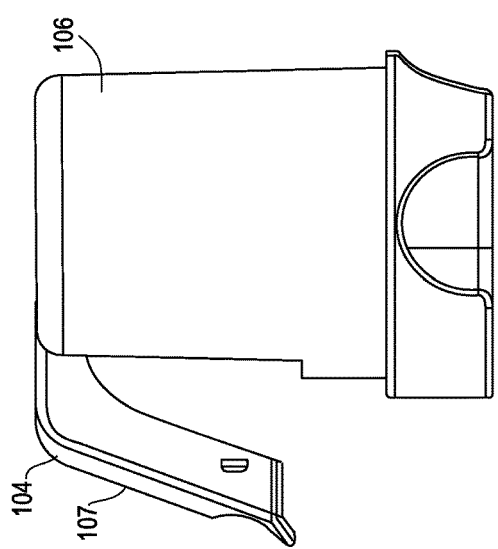

FIGS. 50A, 50B, and 50C illustrate another implementation of a MDI applicator. In the implementation of FIGS. 50A, 50B, and 50C, the MDI applicator includes a lever 104 and a circular housing 106. The circular housing is configured to receive a canister 114 of a MDI 112 and secure the housing 106 against the MDI 112. Additionally, the housing 106 and lever 104 are configured to position the canister against the post 134 of the lever 104 when the housing 106 receives the canister 114 of the MDI 112.

The lever 104 may move between two positions. The lever 104 includes a first portion 105 pivotally connected to the housing, and a second portion 107 extendably connected to the first portion 105, with a protuberance (post 134) extending downwardly from the first portion 105. The second portion 107 is extendable relative to the first portion between first and second positions. In a first, use position, the second portion 107 of the lever 104 is extended away from the housing 106. When the lever 104 is in the first position, the lever 104 operates similar to described above. When a force is applied to the lever 104, the post 134 of the lever 104 transfers the force into a downward force against the canister 114 of the MDI 112. Because the housing 106 is secured to the MDI 112, the downward force against the canister 114 causes the MDI 112 to actuate and release aerosolized medicine.

In a second, storage position, the second portion 107 of the lever 104 is moved towards the housing 106 and locked for storage. A detent 109 on the second portion engages the first portion and holds the first and second portions 105, 107 in the first and second positions. It will be appreciated that when the lever 104 is in a locked position, the lever may not transfer a force to actuate the MDI 112.

FIGS. 1-50 illustrate implementations of MDI applicators that provide a lever to assist a patient in actuating a MDI. The lever transfers forces applied to the lever to a canister of a MDI, thereby causing the MDI to dispense aerosolized medicine for inhalation by a patient.

The embodiments of the invention disclosed herein are presently considered to be preferred, various changes and modifications can be made without departing from the spirit and scope of the invention. As noted, the discussion above is descriptive, illustrative and exemplary and is not to be taken as limiting the scope defined by any appended claims, and all changes that come within the meaning and range of equivalents are intended to be embraced therein.

What is claimed is:

1. A metered dose inhaler applicator comprising:
    a housing defining a cavity shaped to receive a medicament canister; and
    a lever pivotally connected to the housing about a pivot axis, the lever comprising a protuberance adapted to engage the medicament canister, wherein the lever is extendable relative to the housing between a first position, wherein the lever is spaced apart from the housing and is pivotable relative to the housing, and a second position, wherein the lever is positioned adjacent the housing and is prevented from being pivoted relative to the housing, wherein the lever comprises a first portion pivotally connected to the housing, and a second portion extendably connected to the first portion, wherein the protuberance extends downwardly from the first portion, wherein the second portion is extendable relative to the first portion between the first and second positions.

2. The metered dose inhaler applicator of claim 1 further comprising a detent holding the first and second portions in the first and second positions.

3. The metered dose inhaler applicator of claim 1 wherein the second portion is slidably connected to the first portion.

4. The metered dose inhaler applicator of claim 1 further comprising the medicament canister holding a medicine disposed in the housing, wherein the protuberance is positioned against an end of the canister.

5. A metered dose inhaler applicator comprising:
    a housing defining a cavity shaped to receive a medicament canister, the housing comprising a first bottom;
    a lever pivotally connected to the housing, the lever pivotal relative to the housing between an open, use position and a closed, storage position, the lever comprising a second bottom, wherein the first and second bottoms in combination define a co-planar surface when the lever is in the closed, storage position, wherein the co-planar surface is adapted to hold the applicator in an upright position on a flat surface; and
    a carrier moveably coupled to the housing, wherein the carrier is moveable relative to the housing in a vertical direction.

6. The metered dose inhaler applicator of claim 5 wherein the first and second bottoms are positioned below a bottom surface of the carrier when the lever is in the closed, storage position.

7. The metered dose inhaler applicator of claim 5 wherein the lever comprises a protuberance.

8. The metered dose inhaler applicator of claim 7 further comprising the medicament canister holding a medicine disposed in the housing, wherein the protuberance is positioned against an end of the canister.

9. A method of using a metered dose inhaler applicator comprising:
    disposing a canister of medication in a cavity defined by a housing;
    extending a lever from a storage position, wherein the lever is positioned adjacent the housing and is prevented from being pivoted relative to the housing, to a use position, wherein the lever is spaced apart from the housing, wherein the lever comprises a first portion pivotally connected to the housing, and a second portion extendably connected to the first portion, wherein the protuberance extends downwardly from the first portion, and wherein extending the lever from the storage position to the use position comprises extending the second portion relative to the first portion;
    pivoting the lever relative to the housing, when in the use position, about a pivot axis; and
    engaging an end of the canister with a protuberance disposed on the lever and thereby moving the canister relative to the housing.

10. The method of claim 9 further comprising holding the first and second portions in the storage and use positions with a detent.

11. The method of claim 9 wherein the second portion is slidably connected to the first portion.

12. A method of using a metered dose inhaler applicator comprising:
   disposing a canister of medication in a cavity defined by a housing, wherein the housing has a first bottom;
   pivoting a lever relative to the housing between an open, use position and a closed, storage position, wherein the lever comprises a second bottom, wherein the first and second bottoms in combination define a lowermost co-planar surface when the lever is in the closed, storage position;
   disposing the co-planar surface on a flat support surface and thereby holding the applicator in an upright position on the flat surface; and
   moving a carrier relative to the housing to secure the canister in the housing.

13. The method of claim 12 further comprising maintaining the first and second bottoms below a bottom surface of the carrier when the lever is in the closed, storage position.

14. The method of claim 12 wherein the lever comprises a protuberance, and further comprising pivoting the lever relative to the housing when in the open, use position and thereby moving an end of the canister with the protuberance.

* * * * *